United States Patent
Gonzalez-Villasenor

(10) Patent No.: US 6,936,437 B2
(45) Date of Patent: Aug. 30, 2005

(54) METHODS AND COMPOSITIONS FOR PRODUCTION OF RECOMBINANT PEPTIDES

(76) Inventor: Lucia Irene Gonzalez-Villasenor, 626 Charles Street Ave., Baltimore, MD (US) 21204

( * ) Notice: Subject to any disclaimer, the term of this patent is extended or adjusted under 35 U.S.C. 154(b) by 0 days.

(21) Appl. No.: 10/080,919

(22) Filed: Feb. 22, 2002

(65) Prior Publication Data

US 2003/0166062 A1 Sep. 4, 2003

Related U.S. Application Data

(60) Provisional application No. 60/270,839, filed on Feb. 23, 2001.

(51) Int. Cl.[7] .......................... C12P 21/06; C12P 21/04; C07K 1/00; C07K 14/00; C07K 17/00
(52) U.S. Cl. ...................... 435/69.1; 530/350; 530/412; 435/70.1
(58) Field of Search ............................. 435/69.1, 320.1, 435/455, 69.7, 240.2, 254.11, 325, 70.1; 530/350, 412, 300, 324, 21; 539/324; 424/569; 514/2

(56) References Cited

U.S. PATENT DOCUMENTS

| | | | |
|---|---|---|---|
| 4,677,196 A | | 6/1987 | Rausch et al. |
| 4,748,234 A | * | 5/1988 | Dorin et al. .............. 530/412 |
| 5,523,215 A | | 6/1996 | Cousens et al. |
| 5,530,100 A | * | 6/1996 | Darling et al. ............. 530/383 |
| 5,560,937 A | * | 10/1996 | Lee et al. .................. 424/569 |
| 5,834,210 A | * | 11/1998 | Liu et al. ................... 435/7.1 |

OTHER PUBLICATIONS

Couche, Protein Inclusions Produced by Entomopathogenic Bacterium Xenorhadus nematophilus sussp. nematophilus, Aug. 1987, Journal of Bcteriology vol 169, No 11 pp. 5379–5287.*

Moses, Marsha. Troponin I is present in human cartilage and inhibits angiogenesis. Proc. National Acad. Science USA. vol. 96. pp2645–2650. Mar. 1999.*

"Recombinant–DNA–derived bovine growth hormone from Escherichia coli", Keith E. Langley et. al., Eur J. Biochem. 163, pp 313–321, (1987).

"Plasminogen activator inhibitor–1 fused with erythropoietin (EPO) mimetic peptide (EMP) enhances the EPO activity of EMP", Le–tian Kuai et.al., J. Peptide Res., 56, 2000, pp 59–62.

(Continued)

Primary Examiner—Robert A. Wax
Assistant Examiner—Robert B. Mondesi
(74) Attorney, Agent, or Firm—Thomas M. Saunders; Brown Rudnick Berlack Israels LLP

(57) ABSTRACT

This invention provides a method for solubilizing and recovering in bioactive form, a target polypeptide or protein that has been expressed from a host organism in insoluble form. The polypeptide is isolated from the host organism by standard procedures including disrupting the host cell to produce a lysate and recovering the precipitate from the lysate. The precipitate containing the polypeptide is solubilized in a non-denaturant and detergent free non-buffered solubilization solution containing sodium hydroxide between 8 and 10 mM, mannitol between 2 and 5 mM and lactose between 1 and 2 mM. The resultant solubilization preparation contains a biologically active target polypeptide between 1 and 4 mg per ml of solubilization solution. The solubilized polypeptide obtained in this particular manner constitutes the object of the invention. The bioactive solubilized polypeptide is then transferred into an appropriate buffered solution of the desired pH and purified following conventional chromatographic procedures.

40 Claims, 1 Drawing Sheet

OTHER PUBLICATIONS

"Biopharmaceutical formulation", J. Ching Lee, *Current Opinion in Biotechnology*, 2000, 11, pp 81–84.

"Purification and Characterization of Human Interleukin–1 Expressed in *Escherichia coli*", Shirley R. Kronheim et.al., *Bio Technology*, vol. 4, Dec. 1986, pp 1078–1082.

"Expression, renaturation and purification of recombinant human interleukin 4 from *Escherichia coli*", Anita van Kimmenade et. al., *Eur. J. Biochem*, pp 109–114 (1988).

Expression of a biologically active fragment of human IgE ε chain in *Escherichia coli*, Fu–Tong Liu et. al., *Proc. Natl. Acad. Sci. USA*, vol. 81, pp 5369–5373, Sep. 1984.

"Renaturation of *Escherichia coli* Tryptophanase after Exposure to 8 M Urea. Evidence for the Existence of Nucleation Centers", Jacqueline London et. al., *Eur. J. Biochem*. 47, 409–415 (1974).

"Inclusion Bodies from Proteins Produced at High Levels in *Escherichia coli*", Joanna K. Krueger et. al., *Amer. Assoc. for the Adv. Science*, 1990, pp 136–142.

"Refolding of Recombinant Proteins", Tadahiko Kohno et. al., *Methods in Enzymology*, vol 185, pp 18–195, 1990.

"*E. coli* expression and characterization of a mutant troponin I with the three cysteine residues substituted", Lan Kluwe et. al., *FEBS*, vol. 323, No. 1,2, pp 83–88, May 1993.

Production of a biologically active novel goldfish growth hormone in *Escherichia coli*, Soheil S. Mahmoud et. al., *Comparative Biochemistry and Physiological*, Part B, vol. 120, 1998, pp 657–663.

"Intermediates in the Folding Reactions of Small Proteins", Peter S. Kim et. al., *Annu. Rev. Biochem*, 1990, 59, 631–660.

"Refolding and Association of Oligomeric Protiens", Rainer Jaenicke et. al., *Methods in Enzymology*, 1986, 131, pp 218–250.

"Preparation of Biologically Active Platelet–Derived Growth Type BB from a Fusion Protein Expressed in *Escherichia coli*", J. Hoppe et al , *Biochemistry*, 1989, 28, 2956–2960.

"Pathways of Protein Folding", C. Robert Matthews, *Annu. Rev. Biochem*. 1993, 62, 653–683.

"The Purification of eukaryotic polypeptides synthesized in *Escherichia coli*", Fiona A. O. Marston, *Biochem. J*. (1986), 240, 1–12.

"Purification of biologically active simian virus 40 small tumor antigen", Han Bikel et. al., *Proc. Natl. Acad. Sci. USA*, vol. 80, pp 906–910, Feb. 1983.

"Recombinant Chicken and Bovine Growth Hormones Accelerate Growth in Aquacultured Juvenile Pacific Salmon *Oncorhynchus Kisutch*", Jacqueline, A. Gill et. al, *Bio/Technology*, vol 3, Jul. 1985, pp 643–646.

"Renaturation of Enzymes after Polyacrylamide Gel Electrophoresis in the Presence of Sodium Dodecyl Sulfate", Sanford A. Lacks et. al., *The Journal of Biological Chemistry*, vol. 255, No. 15, Aug. 10, 1980, pp 7467–7473.

"Cloning and expression of cDNA for salmon growth hormone in *Escherichia coli*", Susumu Sekine et. al., *Proc. Natl. Acad. Sci. USA*, vol. 82, Jul. 1985, pp 4306–4310.

Purification of Calf Prochymosin (Prorennin) Synthesized in *Escherichia coli*, Fiona A.O. Marston et. al., *Bio/Technology*, Sep. 1984, pp 800–804.

"Expression and equilibrium denaturation of cardiac troponin I: stabilization of a folding intermediate during denaturation by urea", Nihmat Morjana et al., *Biotechnol. Appl. Biochem*. (1998), 28, pp 7–17.

"The Cyanogen Bromide Reaction", Erhard Gross, *Cleavage of Peptide Chains*, pp 238–263.

"Gel Electrophoresis and Isoelectric Focusing of Proteins—Selected Techniques", R.C. Allen et. al., 1984.

"In vitro folding of inclusion body proteins", Rainer Rudolph et. al., *The FASEB Journal*, Jan. 1996, vol 10, pp 49–56.

"Purification and Immunogenicity of Fusion VPI Protein of Foot and Mount Disease Virus", Steven J. Shire et. al., *Biochemistry*, 1984, 23, 6474–6480.

"Examination of calf prochymosin accumulation in *Escherichia coli*: disulphide linkages are a structural component of prochymosin–containing inclusion bodies", J.M. Schoemaker et. al., *The EMBO Journal*, 1985, vol. 4, No. 3, pp 775–780.

"Recovery of soluble human renin from inclusion bodies produced in recombinant *Escherichia coli*", Satish K. Sharma, *Journal of Biotechnology*, 4 (1986) 119–124.

"Isolation and purification of protein granules from *Escherichia coli* cells overproducing bovine growth hormone", Ronald G. Schoner et. al., *Bio Technology*, Feb. 1985, pp 151–154.

"Size and density of protein inclusion bodies", G. Taylor et. al., *Bio/Technology*, vol 4, Jun. 1986, pp 553–557.

"Alteration of catalytic properties of chymosin by site–directed mutagenesis", Junko Suzuki et. al., *Protein Engineering*, vol. 2, No. 7, pp 563–569, 1989.

"Site–directed mutagenesis reveals functional contribution of Thr218, Lys220 and Asp304 in chymosin", Junko Suzuki et. al., *Protein Engineering*, vol. 4, No. 1, pp 69–71, 1990.

Purification of recombinant salmon growth hormone expressed in *Escherichia coli*, Seiji Sugimoto, *Biotechnology Letters*, vol. 13, No. 6, 389–394, (1991).

"Protein engineering to optimize recombinant protein purification", Mathias Uhlen et. al., *Biochemical Society Transactions*, vol 16, pp 111–115, 1988.

"Solubilization and activation of recombinant calf prochymosin from *Escherichia coli*", Fiona A. O. Marston, et al . $613^{th}$ *Meeting, Cardiff*, vol. 13, p. 1035.

"Sequencing of a cDNA encoding the human fast–twitch skeletal muscle isoform of troponin 1", Lei Zhu et. al. *Biochimica et Biophysica Acta* 1217 (1994) 338–340.

"Reconstitution of Lactic Dehydrogenase, Noncovalent Aggregation vs. Reactivation. 1. Physical Properties and Kinetics of Aggregation", Gerd Zettlmeissl et. al., *Physical Properties of LDH Aggregates*, vol 18, No. 25, 1979, 5567–5571.

"Increase of Solubility of Foreign Proteins in *Escherichia coli* by Coproduction of the Bacterial Thioredoxin", Takashi Yasukawa: *The Journal of Biological Chemistry*, vol. 270, No. 43, Oct. 27, 1995, pp 25328–25331.

"Efficient and Rapid Affinity Purification of Proteins Using Recombinant Fusion Proteases", Philip A. Walker et. al., *Bio/Technology*, vol. 12, Jun. 1994, pp 601–605.

"Effects of Low Concentrations of Guanidine, HCI on the Reconstitution of Lactic Dehydrogenase from Pig Muscle in vitro—Evidence for Guanidine Binding to the Native Enzyme", Gerd Zettlmeissl et. al., *Eur. J.Biochem*. 100, pp 593–598 (1979).

"High–level direct expression of semi–synthetic human interleukin–6 in *Escherichia coli* and production of n–terminus met–free product", Hisahi Yasueda et. al., *Bio–Technology*, vol. 8, Nov. 1990, pp 1036–1040.

"Structure, evolution, and regulation of a fast skeletal muscle troponin I gene", Albert S. Baldwin et. al., *Proc. Natl. Acad. Sci.* USA, vol. 82, pp 8080–8084, Dec. 1985.

"Utilization of Zeolite Y in the removal of anionic, cationic and nonionic detergents during purification of proteins", Zoltan Blum et. al., *Biotechnology Techniques*. vol. 5, No. 1, pp 49–54, (1991).

"Principles that govern the folding of Protein Chains", Christian B. Anfinsen, *SCIENCE*, Jul. 20, 1973, vol. 181, No. 4096, pp 223–230.

"Overexpression of human cardiac troponin–I and troponin–C in *Escherichia coli* and their purification and characterization—Two point mutations allow high–level expression of troponin–I", Eman Al–Hillawi et. al., Eur. J. Biochem., 225, pp 1195–1201, (1994).

"Recombinant protein expression in *Escherichia coli*", Francois Baneyx, *Current Opinion in Biotechnology*, 1999, vol. 10, pp 411–421.

"Structure and morphology of protein inclusion bodies in *Escherichia coli*", Gregory A. Bowden, *Bio/Technology*, vol 9, Aug. 1991, pp 725–730.

"Renaturation, purification and characterization of recombinant $F_{ab}$–fragments product in *Escherichia coli*", Johannes Buchner et. al., *Bio Technology*, vol. 9, Feb. 1991, pp 157–162.

Stabilization of Protein Structure by Sugars, Tsutomu Arakawa et. al., *Biochemistry*, 1982, vol. 21, pp 6536–6544.

"Synthesis and cloning of a gene coding for a fusion protein containing mouse epidermal growth factor", G. Allen et.al., *Journal of Biotechnology*, vol. 5, (1987) pp 93–114.

"Denatured States of Proteins", Ken A. Dill, *Annu. Rev. Biochem.*, 1991, vol. 60, pp 795–825.

"Choice of Cellular Protein Expression System", David Gray et. al., *Current Protocols in Protein Science*, (2000), pp 5.16.1–5.16.34.

"Chromatofocusing", Alan Williams, *Current Protocols in Protein Science*, (1997), pp 8.5.1–8.5.10.

"Overview of Protein Purification and Characterization", R.K. Scopes, *Current Protocols in Protein Science*, (1995), pp 1.1.1–1.1.5.

"Strategies for Protein Purification", R.K. Scopes, *Current Protocols in Protein Science*, (1995), pp 1.2.1–1.3.7.

"Conventional Chromatographic Separations", Ben. M. Dunn, *Current Protocols in Protein Science*, (1997), pp 8.0.1–8.1.9.

"Dominant Forces in Protein Folding", Ken A. Dill, *Biochemistry*, vol. 29, No. 31, Aug. 7, 1990, pp 7133–7155.

"Nativelike Secondary Structure in Interleukin–1β Inclusion Bodies by Attenuated Total Reflectance FTIR", Keith Oberg et. al., *Biochemistry*, 1994, vol. 33, pp 2628–2634.

"Efficient renaturation and fibrinolytic properties of prourokinase and a deletion mutant expressed in *Escherichia coli* as inclusion bodies", Gaetano Orsini et. al., *Eur. J. Biochem*, vol. 195, pp 691–697 (1991).

"Culture of Yeast for the Production of Heterologous Proteins", Michael A. Romanos et. al., *Current Protocols in Protein Science*, (1995), pp 5.8.1–5.8.17.

"Solubility as a function of protein structure and solvent components", Catherine H. Schein, Bio/Technology, vol. 8, Apr. 1990, pp 308–317.

"Synthesis of calf prochymosin (prorennin) in *Escherichia coli*", J.S. Emtage, *Proc. Natl. Acad. Sci. USA*, vol. 80, pp 3671–3675, Jun. 1983.

"High–Level Expression in *Escherichia coli* of Biologically Active Bovine Growth Hormone", Henry J. Goerge et. al., *DNA*, vol. 4, No. 4, 1985, pp 273–281.

"Purification of Recombinant Proteins", Paul T. Wingfield, *Current Protocols in Protein Science*, 1997, 6.0.1–6.7.10.

"Reconstitution of Lactic Dehydrogenase. Noncovalent Aggregation vs. Reactivation. 2. Reactivation of Irreversibly Denatured Aggregates", Rainer Rudolph et. al., *Biochemistry*, vol. 18, No. 25, 1979, pp 5572–5575.

"Gene Expression in Recombinant *Escherichia coli* ", Joan Stader, 1995, pp 1–51.

"Gene Expression in Recombinant Bacillus", Matti Sarvas, *Gene Expression in Recombinant Mocroorganisms*, 1995, pp 55–120.

"Use of Stabilizing Additives", Ciaran O'Fagain, *Stabilizing Protein Function*, 1997, pp 69–79.

"Recombinant human insulin–like growth factor II expressed in *Escherichia coli*", Thomas C. Furman et. al., *Bio Technology*, vol. 5, Oct. 1987, pp 1047–1051.

"High–Level Expression and Purification of the Recombinant Diphtheria Fusion Toxin DTGM for PHASE I Clinical Trials", Arthur E Prankel et al , *Protein Expression and Purification*, 16, 190–201, (1999).

"Recovery of soluble, biologically active recombinant proteins from total bacteriallysates using ion exchange resin", Adolf Hoess et al., Bio Technology, vol. 6, Oct. 1998, pp 1214–1217.

"Renaturation of Recombinantion Proteins Produced as Inclusion Bodies", Bernhard E. Fischer, *Biotech. Adv.*, vol. 12, pp 89–101, 1994.

"Refolding and crystallographic studies of eukaryotic proteins produced in *Escherichia coli*", Kiuoshi Nagai et. al., *Biochemical Society Transactions*, 1988, vol. 16, pp 108–110.

"Protein folding intermediates and inclusion body formation", Anna Mitraki et. al., *Bio/Technology*, vol. 7, Jul. 1989, pp 690–697.

"Overview of Protein Expression in *Saccharomyces cerevisiae*", Robert L. Strausberg, *Production of Recombinant Proteins*, 1995, pp 5 6.1–5.6.7.

"Production of recombinant proteins", Paul T. Wingfield, *Current Protocols in Protein Science*, Supplement 20, 2000, pp 5.0.1–5.16.25.

"Fermentation and Growth of *Escherichia coli* for Optimal Protein Production", Alain Bernard et. al., *Current Protocols in Protein Science*, 1995, pp 5.3.1–5.3.18.

"Protein Folding and its Implications for the Production of Recombinant Proteins", Roman Hlodan et. al., *Biotechnology and Genetic Engineering Reviews*, vol. 9, Dec. 1991, pp 47–88.

Reconstitution of Rabbit Skeletal Muscle Troponin from the Recombinant Subunits All Exressed in and Purified from *E. coli*, Setsuko Fujita–Becker et. al., *J. Biochem.*, 114, 438–444, (1993).

"A novel sequential procedure to enhance the renaturation of recombinant protein from *Escherichia coli* inclusion bodies", Bernhard Fischer et. al., *Protein Engineering*, vol. 5, No. 6, pp 593–596, 1992.

"Optimized procedures for purification and solubilization of basic fibroblast growth factor inclusion bodies", D. Estape et al., *Biotechnology Techniques*, vol. 10, No. 7, Jul. 1996, p 481–484.

The Use of Zeolite Y in the Purification of Intra Cellular Accumulated Proteins from Genetically Engineered Cells, Hakan Eriksson et. al, *Biotechnology Techniques*, 1992, pp 239–244.

"Convenient and Efficient In Vitro Folding of Disulfide–Containing Globular Protein from Crude Bacterial Inclusion Bodies", Junichiro Futami et. al., *J. Biochem.*, vol. 127, pp 435–444 (2000).

"Enzyme Applications", M.D. Trevan et. al., *Biotechnology: The Biological Principles*, 1987, pp 203–210.

"Comparing the Refolding and Reoxidation of Recombinant Porcine Growth Hormone from a Urea Denatured State and from *Escherichia coli* Inclusion Bodies", Michael Cardamone et. al., *Biochemistry* 1995, vol. 34, pp 5773–5794.

"The use of EDTA or Polymyxin with Lysonzyme for the Recovery of Intracellular Products from *Escherichia coli*", C.R. Dean et. al., *Biotechnology Techniques*, vol. 6, No. 2 Mar./Apr. 1992 pp 133–138.

"Serodiagnosis of Antibodies to the Human AIDS Retrovirus with a Bacterially Synthesized ENV Polypeptide", Cirilo D. Cabradilla, *Bio/Technology*, vol. 4, Feb. 1986, pp 128–133.

"Aggregation and Denaturation of Apomyoglobin in Aqueous Urea Solutions", Linda R. De Young et. al., *Biochemistry*, 1993, 32, 3877–3886.

"Refolding of recombinant proteins", Eliana De Bernadez Clark, *Biochemical Engineering*, 1998, 9, 157–163.

"Pharmacoeconomics", Joseph F Heyse et. al., *Encyclopedia of Biopharmaceutical Statistics*, 2000, pp 387–401.

"Recombinant DNA Proteins and Drug Discovery", Christopher Hentschel, *Genetically Engineered Human Therapeutic Drugs*, 1988, pp 3–6.

"Chapter 8. Bioproducts and Economics", Harvey W. Blanch et. al., *Biochemical Engineering*, 1996, pp 609–671.

"Solubilization of Protein Aggregates", Fiona A. O. Marston et. al., *Methods in Enzymology*, vol. 182, pp 264–276, 1990.

"Development of an Intravenous γ–Globulm with Fc Activities", Y Masuho et. al. *Vox Sang*, 32: p 175–181 (1977).

"Reversible protection of disulfide bonds followed by oxidative folding render recombinant hCGβ highly immunogenic", Asok Mukhopadhyay, *Vaccine*, 18 (2000) 1802–1810.

"Refolding of Therapeutic Proteins Produced in *Escherichia coli* as Inclusion Bodies", Satoru Misawa et. al., *Biopolymers*, 51, 297–307, (1999).

"Global Supression of Protein Folding Defects and Inclusion Body Formation", Anna Mitraki et. al., *Science*, vol. 253, pp 54–58.

"Structural characterization of the human fast skeletal muscle troponin I gene (TNN12)", Antony J. Mullen et. al., *GENE*, 242, (2000) 313–320.

\* cited by examiner

METHODS AND COMPOSITIONS FOR PRODUCTION OF RECOMBINANT PEPTIDES

This application claims priority from Provisional Application Ser. No. 60/270,839 filed Feb. 23, 2001, incorporated in its entirety by reference.

FIELD OF THE INVENTION

This invention entails a method for solubilizing and recovering, in bioactive and isolated form with retained native state configuration, target peptide from a host organism in which the heterologous polypeptide is present in insoluble form. Broadly this method comprises (i) disrupting the host cell to produce a lysate (ii) recovering lysate precipitate containing the polypeptide (iii) resuspending the lysate precipitate in a denaturant-free, non-buffered solubilization solution to produce a solubilization preparation that optimally comprises sodium hydroxide between about 8 and about 10 mM, Mannitol between about 2 and about 2.5 mM, Lactose between about 1 and about 2 mM and the target peptide between about 1 and about 4 mg peptide per ml solubilization solution, wherein the resultant solubilization preparation has a pH of between about 9 and about 11.2; (iv) recovering supernatant from the solubilization preparation containing non-denatured target peptide. The invention further comprises isolated insoluble proteins in bioactive form and native state configuration.

BACKGROUND OF THE INVENTION

Many peptides, polypeptides, and proteins (collectively, "target peptide(s)") can be produced via recombinant means. Recombinant protein production has been established in a variety of expression systems. Such expression systems, include strains of bacteria and fungi as well as mammalian and baculovirus or insect cells. These expression systems are not without technical problems. One problem is the recovery or separation of the target peptide from the system as a whole.

Isolating a target peptide from native or host cell/expression system proteins and other cellular products is a significant hurdle in expression system utility. Consider, for example, yeast systems employed for synthesis of target peptides such as human growth hormone, interferons and the like. The biological activity (and potential utility) of the target peptide is dependent upon the target peptide's assumption of specific secondary and tertiary structural conformations. In many instances, the secondary and tertiary structural conformation sought is that duplicative of a the native state configuration.

In some expression systems, target peptide accumulate within the host cells as insoluble aggregates. Recombinant proteins expressed are known to accumulate in cytoplasm as insoluble aggregates known as inclusion bodies. (F. A. O. Marston, Biochem. J. 240:1–12 (1986); C. H. Schein, Biotechnology 7:1141–1149 (1989)). This is particular noted in bacteria and yeast expression systems. The effectiveness of an expression system turns, in part, on recovery of Target peptide in a soluble active form with particular reference to native state configuration Peptides, polypeptide, and proteins are chains of amino acids linked by peptide bonds. As a general biological principal, the behavior of a peptides, polypeptide, or proteins in a chemical or biological system is effected by or related to its (i) amino acid composition, (ii) configuration (i.e., the three dimensional arrangement of amino acid side groups in a particular order) and (iii) conformation (i.e., the three dimensional arrangement of side groups in amino acids which can freely rotate into different positions without breaking bonds). In a given biological system a peptides, polypeptide, or protein of that system is folded into a specific three dimensional structure. Without being bound by ant particular theory, it is believed that a particular three dimensional structure is determined by the thermodynamic forces, stearic considerations, covalent disulfide bonds, if any, and noncovalent interatomic forces (i.e., charge, hydrogen bonding and hydrophobic interactions).

In the isolation of target peptide from recombinant expression systems, preservation of bioactivity and or native state configuration has been a problem in prior art methods. A target peptide that is recovered in a non-native state configuration is potentially of altered bioactivity. Altered bioactivity is variously presented as more active in some reactions and less active in others. In some instances, a longer half-life will enhance the total activity of a target peptide even if the instantaneous activity is less than a naturally occurring peptide. A number of theories have been advanced to explain target peptide resulting from expression systems in non-native state configuration. One view is that the environment of the expression system does not provide conditions for proper "folding" of the target peptide. Reports in the art suggest that the tertiary structure of peptides and proteins is a direct result of the sequence, (secondary structure). Under some conditions, peptides and proteins in an inactive configuration of configuration of reduced bioactivity configuration are induced to adopt (more) bioactive or native state configurations.

Again, without being bound by any particular theory, it is thought that some biologically inactive peptides, polypeptides or proteins are inactive due to being "frozen" in a particular conformation as a result of "extraneous" or "incorrect" cystine disulfide bonds. In some instances "incorrect" cystine disulfide bonds arise during target peptides expression in a given expression system. By this theory, as the number of cysteine residues in Target peptides increases, the probability that disulfide bonds will properly form decreases. A disulfide bond is a covalent cross-link between two cysteine residues that have been oxidized to form cystine. Disulfide bonds are cleaved by reducing agents [e.g., DTT or beta-mercaptoethanol] to form sulfhydryl or thiol groups which are rather unstable. Disulfide bonds are largely permanent in the absence of unusual chemical manipulation. A denaturation/renaturation step is unlikely to restore bioactivity when the basis of inactivity is non-native state disulfide bonds. Disulfide bonds largely exclude further conformational changes and thus exclude adoption of native state configuration (or some other desirable tertiary configuration).

Reported difficulties associated with recovery of biologically active polypeptides containing multiple disulfide bonds have been so severe that polypeptide analogs of significant proteins have been "designed" for expression on the basis of their greater potential for recovery in a bioactive state absent incorrect disulfide bonds rather than for enhanced or prolonged therapeutic activity. As one example, the general inability to recover troponin subunit polypeptides in biologically active form prompted construction of genes for expression of various troponin analogs wherein undesired disulfide bond formation was precluded by replacing cysteines with other amino acids. Fujita-Becker et al., "Reconstitution of rabbit skeletal muscle troponin from the recombinant subunits all expressed in and purified from *E. coli*," *J. Biochem.* 114:438–44 (1993). For polypeptides with two or more cysteine bonds, however, such techniques will be of limited effect.

Note is made of the following publications:
1. Stryer, *Biochemistry*, 2d Ed., 32–36 (1981).
2. U.S. Pat. No. 5,340,926, Lowe et al. "Process for the recovery of recombinantly produced protein from insoluble aggregate."
3. U.S. Pat. No. 4,511,502, Builder et al. "Purification and activity assurance of precipitated heterologous proteins"
4. U.S. Pat. No. 4,511,503, Olson et al., "Purification and activity assurance of precipitated heterologous proteins."
5. De Bernardez, "Refolding of recombinant proteins." *Curr. Opin. Biotechnol.* 9:157–163, (1998)
6. Fischer, "Renaturation of recombinant proteins produced as inclusion bodies." *Biotech. Adv.* 12:89–101 (1994).
7. Guiseet al., "Protein folding in vivo and renaturation of recombinant proteins from inclusion bodies." *Mol. Biotechnol.* 6:53–64 (1996)
8. Hlodan et al., "Protein folding and its implications for the production of recombinant proteins." *Biotechnol. Genet. Eng. Rev.* 9:47–88 (1991)
9. Jaenicke R, et al. "Refolding and association of oligomeric proteins." *Meth. Enzymol.* 131:218–50 (1986)
10. Marston, "The purification of eukaryotic polypeptides synthesized in *Escherichia coli.*" *Biochem. J.* 240:1–12 (1986).

Transgenic plants have proven to be a versatile expression system, successfully used for antibody fragments, IgG and secretory IgA antibodies. Plants are higher eukaryotic organisms with an endomembrane system. Plants fold and assemble recombinant proteins using protein chaperones that are homologous to those in mammalian cells. Notably, plant systems glycosylate proteins.

11. Sanchez_Navarro et al., "Engineering of alfalfa mosaic virus RNA 3 into an expression vector," *Arch Virol.* 146(5):923–39 (2001).
12. Kusnadi et al., "Production and purification of two recombinant proteins from transgenic corn." *Biotechnol Prog* 14(1):149–55 (1998)
13. Streatfield et al., "Medical molecular farming: production of antibodies, biopharmaceuticals and edible vaccines in plants," *Trends Plant Sci* 6(5):219–26 (2001).

Eggs systems, conveniently chicken eggs systems, produce recombinant protein with particular reference to human therapeutics such as antibodies.

14. Mohammed et al., "Deposition of genetically engineered human antibodies into the egg yolk of hens," *Immunotechnology* (1998) 4(2):115–25.
15. Zajchowski, et al., "Incorporation of genetically modified cells in chicken chimeras," *Methods Mol Biol* 36:391–7 (2000).

Also
16. Suttnar et al., "Procedure for refolding and purification of recombinant proteins from *Escherichia coli* inclusion bodies using a strong anion exchanger." *J. Chromatogr. B. Biomed. Appl.* 656:123–6 (1994).

In the isolation of target peptides from a given expression system, protein solubilization from inclusion bodies is a significant concern. In some systems, protein aggregates are solubilized with chaotropic reagents such as guanidine hydrochloride and urea; with thiol compounds such as beta-mercaptoethanol and dithiothreitol; with inorganic salts such as potasium or sodium thiocyanate, lithium bromide and sodium iodide; organic solvents; formamide, dimethylformamide, dichloro- and trichloroacetic acids and their salts; powerful detergents such as sodium dodecyl sulphate and cetyltrimethylammonium chloride; increasing temperature, strong alkalis with salts or a combination of chaotropic reagent and strong alkali solutions; and high pressure and ultrasonic homogenization also denature protein molecules.

All these chemical compounds and physical forces cause dissociation of S—S bonds, which are essential for maintaining the conformation and rigidity of active sites, and biological activity. Furthermore, strong alkalis cause hydrolysis of peptide bond or amides, hydrolysis of arginine, loss of amino acids by alpha- and beta-elimination and racemization, and formation of double bonds or modified amino acids. Salts such as sodium chloride, sodium acetate and sodium sulfate compete with the proteins and stabilizers for the water molecules and their large positive change in chemical potential destabilizes the system causing protein precipitation rather than solubilization. It has been reported that 6M Guanidine Hydrochloride and 8 M Urea are commonly used to cause such S—S bond or disulfide bridge dissociation. Dissociation of these essential S—S bonds leads to loss of biological activity of some proteins. Thiol compounds such as Beta-mercaptoethanol and Dithiotreitol (DTT) cleave disulfide bonds by reduction of S—S bonds to the —SH form of cysteine residues in the denatured protein. Such compounds are usually added to solutions of chaotropic reagent during denaturation. Furthermore, in methods constituting the prior art, to refold the recombinant polypeptide into a biologically active product, the denaturant must be removed from the denatured protein, a slow, complex and difficult process, which usually results in protein precipitation and low yields. It is also required that SH groups are re-oxidized during refolding to produce a biologically active polypeptide. As reported, this is achieved using Cysteine and Cysteamine, or Glutathione in its oxidized and reduced form to provide the appropriate redox potential allowing the formation and reshuffling of disulfides. The removal of the denaturant by dialysis or direct dilution often results in protein re-aggregation rather than fold resulting in accumulation of inactive species and further complicating the purification process. To slow down the aggregation process refolding is usually performed at very low protein concentrations, in a range of 10–100 ug per ml. In addition, only small quantities of this material contain biological activity. Consequently the solubilization and refolding processes have been the main problem in the production of high quantities of recombinant polypeptides and the many methods described cannot be applied to any polypeptide as general methods. In summary, the solubilization of inclusion bodies with strong chaotropic reagents and/or strong alkalis, detergents, salts and/or high temperatures as well as the removal of denaturants and the subsequent protein dilution in the presence or absence of thiol compounds to induce refolding of the protein into a biologically active form, have been the rule for recovery of recombinant proteins that have been over-expressed in microbial hosts.

SUMMARY OF THE INVENTION

The method of the present invention avoids chaotropic reagents, strong alkalis, high temperature, detergents, salts and other additives. It further avoids dilution of solubilized recombinant proteins to low protein concentration to obtain a biologically active protein form. The present invention provides methods of (i) solubilization of protein aggregates from inclusion bodies of host cells such as bacteria and (ii) of stabilization of biological active recombinant proteins from crude extracts or isolated recombinant proteins.

In particular embodiments the invention relates to novel methods to solubilize recombinant polypeptides from "isolated inclusion-body labile-insoluble proteins", (see definition) inclusion bodies produced by fermentation in the bacteria, *Escherichia coli,* and to stabilize the solubilized recombinant proteins to preserve their biological activity. These methods of inclusion bodies solubilization and protein stabilization for maintaining protein solubility and biological activity are broadly applied to monomeric polypeptides. In the procedures described here, the solubilization of inclusion bodies is carried out in an aqueous solution called the 'solubilization solution' at elevated pH, preferably NaOH between about 8 and 1 about 0 mM and pH of between about 10.5 to about 11.0, (generally avoiding pH in excess of about 11.2) and at low pH, preferably with HCL between about 10 to about 20 mM and pH between about 2.2 to about 2.6 at protein concentrations of between about 2 to about 10 mgP/ml depending on the pH. The solubilization solution includes stabilizers preferably Mannitol between about 2 and about 2.5 mM and Lactose between about 1 and about 2 mM. The time of solubilization of inclusion bodies is dependent on the overall charge of the protein, pH, compounds in the solvent, and temperature, and are easily determined empirically for each different polypeptide following the procedure. Stabilization of crude and isolated biologically active recombinant proteins is carried out by dialysis of about 48 hours or by ultrafiltration/diafiltration into an aqueous solution named the "stabilization solution" containing about 30 to about 40 mM sodium bicarbonate pH about 8.0 or about 10 to 20 mM sodium phosphate pH about 8.0 and about 5 to about 10 mM lactose or sucrose and/or about 10 to about 100 mM mannitol or about 2% to about 5% glycerol at protein concentrations of between about 2 and about 10 mg P/ml with or without about 10 mM methionine or cysteine, depending on the polypeptide. The osmolality of the final product (isolated protein preparation) is increased to physiological levels by adding appropriate amounts of sodium chloride. Recombinant polypeptides oxidize and refold into biologically active forms with or without exogenous reducing agents, depending of the polypeptide, in the presence of the "stabilization buffer."

The stability and solubility of recombinant proteins that have been solubilized at high concentrations with chaotropic reagents such as 8 M Urea and 6 M Guanidine hydrochloride (prior art) is also reestablished by transferring the denatured protein into the "stabilization buffer." In the presence of this solution the proteins oxidize and refold into biologically active forms with or without exogenous reducing agents, depending on the protein.

The methods described herein are used as methods for the solubilization and stabilization of recombinant proteins that are sequestered in inclusion bodies that have been obtained by fermentation in a microbial host such as bacteria or yeast. Particular note is made of the hosts *Escherichia coli* and *Saccharomyces cerevisiae.* The methods are applied to monomeric proteins. Reference is made to monomeric proteins in the range of about 16 to about 60 KDa with high and low content of hydrophobic amino acid residues, a high level of positively and/or negatively charged amino acid residues and several cysteine residues. The procedures described herein have been particularly effective in the solubilization of inclusion bodies containing fish somatotropins and prolactin, and human fast twitch skeletal muscle Troponin I. "Recombinant protein" or "recombinant polypeptide" is usefully derived from eukaryotic organisms (e.g. higher and lower vertebrates, mammalian and non-mammalian). The term "recombinant polypeptide" is meant to include, but not limited to, monomeric proteins of commercial and therapeutic value such as somatotropins (growth hormones), somatotropin-like proteins (prolactin, somatolactin and placental lactogen), angiogenic inhibitors (Troponin, Endostatin), cytokines (IL-2, 4, 6, 12) and many other polypeptides.

The present invention includes a method for solubilizing and recovering, in active and isolated form, a target peptide from a host organism in which the target peptide is present in insoluble form, which comprises:

disrupting the host cell to produce a lysate;

recovering lysate precipitate containing the target peptide;

resuspending the lysate precipitate in a denaturant-free, non-buffered solubilization solution to produce a solubilization preparation that comprises 1) a concentration of sodium hydroxide between about 8 and about 10 mM and 2) a concentration of polypeptide between about 1 and about 4 mg polypeptide per ml solubilization solution, wherein the resultant solubilization preparation has a pH of between about 9 and about 11.2; and recovering supernatant from the solubilization preparation containing bioactive target peptide.

In some embodiments the solubilization solution is substantially free of detergent. It is contemplated to further purify the resulting bioactive target peptide. In particular embodiments the solubilization preparation has a pH of between about 10.5 and about 11.2, and further the solubilization preparation comprises a concentration of sodium hydroxide between about 8.5 and about 9.5 mM. In some instances the solubilization preparation comprises a concentration of polypeptide between about 2.5 and about 3 mg polypeptide per ml solubilization solution, and optionally the solubilization solution further comprises a stabilizing compound. Stabilizing compound at concentration between about 1 and about 20 mM is noted, and optionally a second stabilizing compound. Useful as stabilizing compound is a stabilizing sugar such as lactose, stabilizing polyol, stabilizing amino acid or stabilizing polymer.

In the practice of the method host organisms include bacteria or yeast, with particular reference to *Escherichia coli, Bacillus thuringiensis* and *Saccharomyces* populations or cells.

The method includes practice wherein the target peptide is present within the host organism in inclusion bodies. Particular target peptides of the method are troponin or a subunit of troponin such as Troponin I.

The invention yet further includes formulating target peptide, comprising:

(i) dialyzing or ultrafiltering the polypeptide into an aqueous stabilization buffer comprising a stabilizing compound, (ii) dispensing the target peptide into vials.

In the practice of this method one particular target peptide is troponin. In the method the stabilization buffer usefully comprises buffer salt at concentration between about 5 and 40 mM, and further wherein the stabilizing compound is a sugar or polyol. Particular reference is made to the stabilizing compound being a sugar at concentration between about 2 to 12 mM, and the stabilizing compound being a polyol at concentration between about 5 to 100 mM.

In addition the invention comprises a method for solubilizing and recovering, in bioactive and isolated form, a target peptide from a host organism in which the target peptide is present in insoluble form, which comprises:

(a) disrupting the host cell to produce a lysate;

(b) precipitating said lysate (c) recovering lysate precipitate containing the polypeptide (d) resuspending the lysate precipitate in a denaturant-free non-buffered solubilization solution to produce a solubilization preparation that comprises
   1) hydrogen chloride at between about 10 and about 20 mM and
   2) polypeptide at between about 1 and about 4 mg precipitate per ml solubilization solution, and
   3) pH of between about 2.0 and about 3.0; and
(d) recovering active the target peptide as supernatant from the solubilization preparation of (c).

In such method a further step is adjusting the pH of the supernatant to pH 9.5 with NaOH, with particular refererrnce to the solubilization solution being free of detergent. A specific solubilization preparation of the method has a pH of between about 2.2 and about 2.8, and further comprises a concentration of hydrogen chloride between about 10 and about 20 mM. In such method the solubilization preparation usefully comprises a concentration of polypeptide between about 2.5 and about 3 mg polypeptide per ml solubilization solution, or a concentration of polypeptide between about 1.8 and about 2 mg polypeptide per ml solubilization solution.

In some embodiments of the method the solubilization solution further comprises a stabilizing compound with specific reference to a concentration between about 1 and about 20 mM, and optionally, a second stabilizing compound. Noted stabilizing compounds of the method include sugar such as mannitol or lactose, polyol, amino acid or polymer. The method includes the host cell being bacteria or yeast, with particular reference to *Escherichia coli, Bacillus thuringiensis* and *Saccharomyces* as single cells or in populations. In this method the heterologous polypeptide as a target protein is usefully present within inclusion bodies within the host cell or population.

The invention comprises a method of isolating recombinant proteins comprising:
   providing a non-buffered solution that comprises a stabilizing compound and hydrogen chloride between about 10 and about 20 mM;
   producing a protein solution by adding to the non-buffered solution a recombinant polypeptide between about 1 and about 4 mg polypeptide per ml non-buffered solution, wherein the protein solution has a pH of between about 2.0 and about 3.0;
   increasing the pH of the protein solution to between about 4 and 5 using 1N NaOH;
   centrifuging the protein solution and recovering precipitate-free supernatant; and
   adjusting the pH of the supernatant to between about pH 9 and 10.5 with 1N NaOH
      retaining the supernatant comprising isolated target protein at least about 10% more pure than the isolated target protein in aggregate form.

The invention yet further comprises a method for isolating recombinant proteins comprising:
   providing a non-buffered solution that comprises a stabilizing compound and sodium hydroxide between about 8 and about 10 mM;
   producing a protein solution by adding to the non-buffered solution a recombinant polypeptide between about 1 and about 4 mg polypeptide per ml non-buffered solution, wherein the protein solution has a pH of between about 9 and about 11.2;
   lowering the pH of the protein solution to between about 4 and 5 using 1N NaOH;
   centrifuging the protein solution and recovering precipitate-free supernatant; and
   adjusting the pH of the supernatant to between about pH 9 and 10.5 with 1N NaOH
      retaining the supernatant comprising isolated target protein at least about 10% more pure than the isolated target protein in aggregate form.

In n additional embodiment, the invention comprises a method for preparing bioactive recombinant polypeptide in a chaotrope-containing solution, comprising:
   decreasing the concentration of the chaotropic agent in the chaotrope-containing solution by dialyzing the chaotrope-containing solution against a renaturing buffer of pH between about 9 and about 11.2 and buffer concentration between about 10 and about 50 mM, wherein the renaturing buffer further comprises a stabilizing compound;
   chromatographically purifying the protein; and
   dialyzing the isolated protein against an aqueous stabilization buffer comprising a stabilizing compound.

In this method, specific stabilizing compounds include a sugar or polyol. Particular reference is made to a sugar between about 2 and about 12 mM, and a polyol between about 5 and 100 mM.

DESCRIPTION OF THE INVENTION

Figure 1:
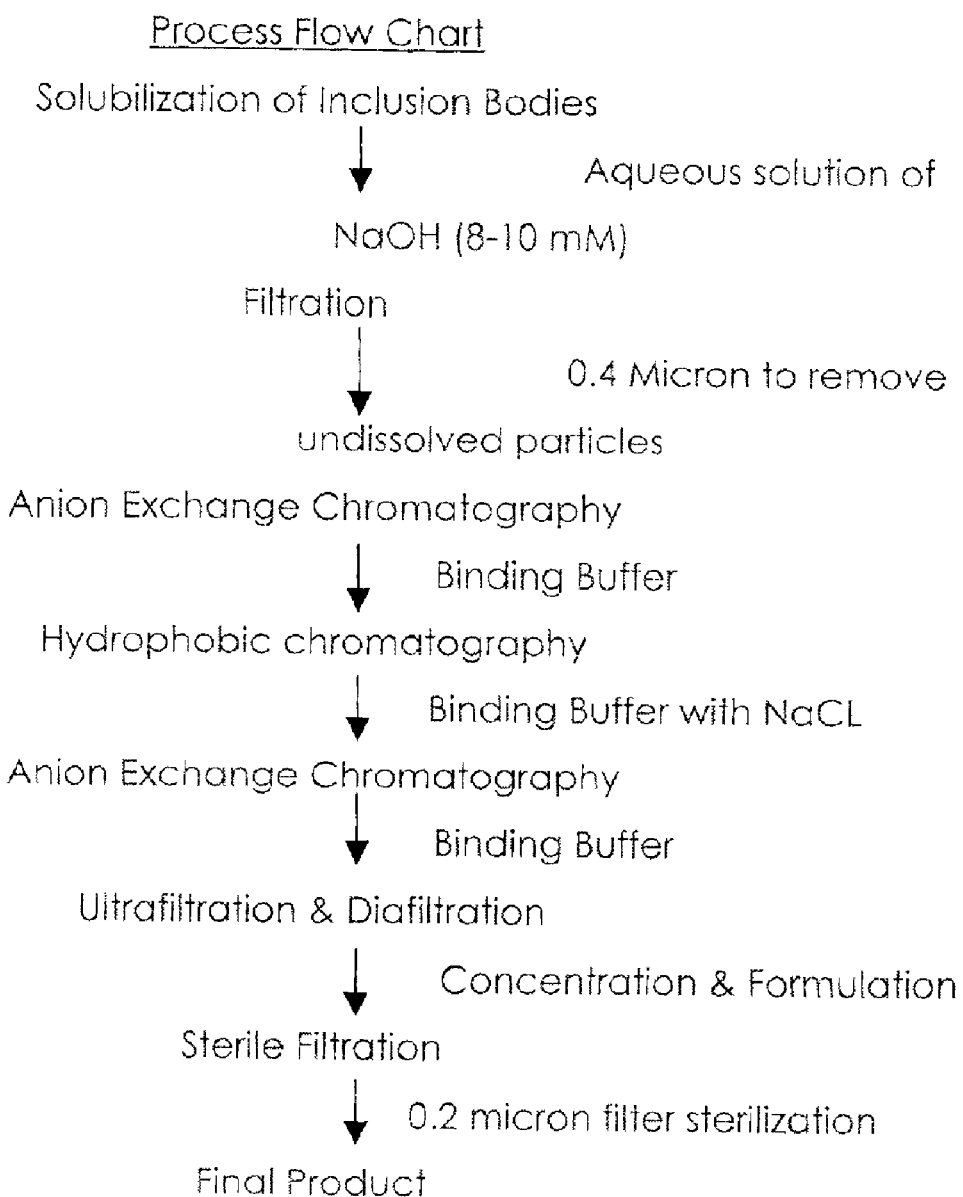
FIG. 1 presents a general schematic diagram of production of a biologically active recombinant protein from inclusion bodies expressed in *E. coli* by fermentation.

This invention will be better understood with reference to the following definitions:

A. "Stable-Solubilizing" shall mean dissolving protein in an aqueous fluid which maintains the protein in a dissolved state, preserves its biological activity and is thermodynamically stable.

B. "Recovering" shall mean that the protein is recovered from inclusion bodies in a not denatured form but has an altered tertiary structure, which differs from that of their native states. After solubilization, the recovered protein is converted into its biologically active form.

C. "Bioactive" shall mean a polypeptide in its native form capable of effecting its intended in vivo physiological response. Biological activity is determinable in vitro or in vivo by carrying out suitable bioassays to determine the potency or activity of protein preparations. Bioactivity is determined for a given protein by any of a variety of known methods including bioassays specific for each protein. By way of example, the colorimetric determination of cellular acid phosphatase activity is described by Connolly et al., *J. Anal. Biochem.* 152:136–140, (1986).

D. "Folding" shall mean to recover the native tertiary structure of the non-denatured reduced protein by oxidation of sulfhydryl groups.

E. "Oxidation" shall mean the formation of correct intramolecular disulfide bonds to obtain the stable native conformation to ensure biological activity.

F. "Extraneous" or "incorrect" cystine disulfide bonds shall mean the formation of incorrect cross-links between the cysteine residues of a polypeptide chain. Ulncorrect cross-links are the result of a lack of adjustment of each single bond in the chain to various constraints that act upon the freedom of rotation around the single bonds of the polypeptide chain. Constraints include the rigid planar nature of the peptide bond, the number and location of hydrophobic and hydrophilic residues in the sequence and the number and location of positive and negatively charged R groups.

G. "Denature" is a term which historically meant the combined unfolding and cleavage of disulfide bonds to yield a random form of a polypeptide chain with loss of biological activity. Typically, denaturing agent is added to a sample of peptide or protein. A typical denaturing agent disrupts non-covalent interatomic forces and unfolds the molecule. If desired, the denatured peptide or protein is then renatured by removal or dilution of the denaturing agent so that the peptide or protein adopts its native state configuration. Addition of detergents or heating are common forms of denaturing protein.

H. "Naturation" or "renaturation" are historically used terms meaning establishing or maintaining the native state configuration of the protein, and particularly refers to the folding and oxidation. Naturing is it the activity of folding and oxidizing or the end state of a heterologous protein to its native state configuration consistent with bioactivity.

Strong denaturing solutions shall include guanidine hydrochloride or sodium thiocyanate in high concentrations of approximately 4–9 M or detergents such as sodium dodecyl sulfate (SDS) or Triton-X-100 in concentrations of about 0.01 to about 2%. Weak denaturing solutions include urea and lower concentrations of strong denaturing solutions. Among the weak reducing agents are β-mercaptoethanol, dithiothreitol and reduced glutathione I. "Alkaline" or "acidic aqueous solutions" refers to solutions prepared with water, NaOH (about 8 to about 10 mM) or HCl (about 10–20 mM) and low concentration of stabilizers like Mannitol (about 2 to 2.5 mM) and Lactose (about 1 to about 2 mM). These aqueous solutions when used with crude (unisolated) bacterial inclusion bodies should not contain salts (sodium chloride, sodium acetate or sodium sulfate) since they destabilize the system due to their large positive change in chemical potential. This change in chemical potential is thermodynamically unfavorable and leads to protein association, aggregation and precipitation.

J. "Buffer" shall mean a substance that helps a solution maintain a certain pH even though hydrogen ions are being added to or subtracted from the solution. Buffers act by either taking up the excess hydrogen ions or by releasing more as needed. Salts of weak acids and bases are buffers It is noted that while amino acids and proteins also act as buffers, in the instant disclosure, the references to the use of presence of buffers excludes amino acids or proteins unless expressly included.

K. "Aqueous stabilization buffer" shall mean a buffered salt, such as sodium bicarbonate between about 30 and 40 mM, sodium phosphate between about 10 and 30 mM with a pH between 8.0 to 8.3, and stabilization buffer also contains one or more stabilizers, which include a sugar (e.g. lactose) between about 5 and 12 mM, or a polyol (e.g. mannitol at about 10–100 mM or glycerol between about 2% and about 10%).

L. "Osmolarity" refers to the concentration of osmotically active particles in solution expressed in terms of osmoles of solute per Liter of solvent. Osmolarity is identical (steady state conditions) in all body fluid compartments.

M. "Physiological saline" refers to an isotonic solution with a physiologic pH in which the concentration of particles in solution (milliosmolar units: 1 mOSM=$10^{-3}$ osmoles/L) are adequate (biocompatible) for the normal functioning of cells in organisms.

N. "Alkaline solubilization solutions" shall mean water containing low concentrations of alkali and stabilizers. In particular embodiments these include sodium hydroxide or potassium hydroxide between about 8 and about 10 mM. In another embodiment, they include sodium hydroxide between about 8.5 and about 9.5 mM. The alkaline solubilization preparation upon dissolution of recombinant polypeptide or inclusion bodies, has a pH of between about 9 and about 11.2; in one embodiment the pH is between about 10.5 and 11.2.

O. "Acidic solubilization solutions" shall mean water containing low concentrations of acid and stabilizers. In Particular embodiments these include hydrogen chloride (HCl) between about 10 and about 20 mM. The resultant acidic solubilization solution having a pH of between about 1.8 and about 3.0. In a particular embodiment, the acidic solubilization preparation has a pH of between about 2.2 and about 2.8.

P. "Disulfide adduct forming" shall mean denaturing a polypeptide in a strong denaturing solution containing a reducing agent. The reducing agent reductively dissociates disulfide bonds. The polypeptide is then treated with an oxidizing agent in the presence of sulfite ion to form disulfide adducts. The strong denaturing solution is then replaced with a weak denaturing solution to permit remolding. Disulfide linkages are reformed using sulfhydryl compounds such as cysteine or reduced glutathione, in the presence of the corresponding oxidized (disulfide) form, but with the reduced form in excess. Compounds disclosed for include oxidized glutathione, cystamine and cysteine.

Q. "Reducing agent" shall mean a compound maintains sulfhydryl groups in the reduced state and reduces disulfide intra- or intermolecular bonds. Reducing agents include glutathione, dithioerythritol, dithiothreitol (DTT), or mercaptoethanol. A reducing agent is added to the solubilization solution for particular proteins to preserve maximal bioactivity.

If the protein product of a method of the invention using solutions free of reducing agents is found to have low biological activity in an appropriate bioassay, the procedure may be repeated with solubilization and stabilization solutions containing one or more reducing agents at concentrations such as are routine in the art of protein purification. For example, DTT may be used in concentrations of 0.1–10 mM, mercaptoethanol at 1–20 mM or about 2% of final solution, or glutathione at 1–4 mM.

Protein structure is organized at four levels: primary, secondary, tertiary and quaternary. Primary structure shall mean, the sequence of amino acids in the protein. A protein amino acid chain starts with an amino acid with a free amino group (the N terminus) and ends with one with a free carboxyl group (the C terminus). It is believed that the distribution in the chain of amino acids with charged side-groups causes it to be coiled or folded into alpha helices, beta sheets and turns to yield the common secondary structure. The arrangement of all the protein atoms in space, without regard of relationships with neighboring molecules or subunits determines the tertiary structure, which is the overall three-dimensional shape of the polypeptide chain. The quaternary structure of a protein molecule is the arrangement of its subunits in space, in non-covalent association, and the ensemble of its intersubunit contacts and interactions, without regard to the internal geometry of the subunits.

R. "Isolated inclusion-body labile-insoluble proteins" shall mean protein aggregates of high density that can be recognized by phase contrast microscopy and that are produced by fermentation in bacterial cells. These proteins are recovered in a biologically active form by solubilization into low concentration "alkaline or acidic solubilization solutions" (see definition above).

The term "isolated" is used in distinction to "purified" because after solubilization the protein still contains some contaminants. Isolated shall be understood to mean at least about 60% by weight of the aggregate comprises target protein, and preferably at least about 70% by weight. Inclusion bodies are protein aggregates with an altered tertiary structure. These will return to active or native state until after solubilization. Later solubilization of isolated target protein aggregates and alkaline precipitation of contaminants increase the content of target protein by at leat about 10% (relative to the isolated target protein in aggregate form).

S. "Dialysis" or "Ultrafiltration/Diafiltration" refers standard methods for exchanging the solubilization solution and/or the purification buffers into the formulation solution to stabilize the solubilized protein and/or the final purified product.

T. "Recombinant protein" in reference to a means of production shall mean the product of expression by fermentation of a recombinant gene that has been cloned or inserted by mechanical or other artificial means into an expression vector and/or introduced by transformation into a bacterial host such as E. coli. Recombinant protein is often expressed in an insoluble non-native form. The term further is meant to include, but not limited to, any mammalian and non-mammalian monomeric protein.

U. "Host organisms" (also termed host cells) refers to organisms genetically modified by transformation with a recombinant vector. This is optionally propagated and its DNA expressed. The term also includes any progeny of the host cell or organism. Biologically functional viral and plasmid DNA vectors capable of expression and replication in a host included within the term host organism. Such vectors are used to insert or clone nucleotide sequences.

In general, host organisms employed as expression vectors contain promoter sequences which facilitate the efficient transcription of the inserted eukaryotic genetic sequence. An expression vector typically has associated with the genetic sequences of interest an origin of replication, a promoter, and a terminator, as well as specific genes which are capable of providing phenotypic selection of the transformed cells.

V. "Heterologous polypeptide" shall be broadly understood to mean those peptides, polypeptides and proteins produced by an organism that is not the wild type source of those proteins. For example, bacteria have been genetically engineered to produce human growth hormone and bovine (i.e., cow) somatotropin. In most instances a heterologous peptide is one not native to the host species. Heterologous protein shall be understood to include any protein coded for by heterologous DNA and expressed by a host cell transfected with the heterologous DNA or capable of such expression. In some instances and for efficiency of terminology, a heterologous protein will include a protein elaborated by a host organism, and "native to that organism, but "over produced" as a result of fermentation or genomic signaling.

W. "Peptide" shall mean two or more amino acids covalently joined by peptide bonds. An oligomer component of a polypeptide. A dipeptide, for example, consists of two (di) amino acids joined together by a peptide bond or linkage. By analogy, this structure would correspond to two joined links of a chain. Polypeptide shall mean a molecular chain of amino acids linked by peptide bonds. Polypeptide is synonymous with protein. Peptide, polypeptide and protein are terms referencing peptides of increasing size. For convenience herein, the terms are used interchangeably unless distinguished.

X. "Target peptide" is a collective term for any peptide, polypeptide or protein being specifically sought or isolated.

During their synthesis (after emerging from cell's ribosome), proteins may also be phosphorylated (i.e., a "phosphate group" is added to the protein molecule), glycosylated (i.e., one or more oligosaccharides is added onto the protein molecule), acetylated (i.e., one or more "acetyl groups" is added to the protein molecule), farnesylated (i.e., a "farnesyl group" is added to the protein molecule), ubiquinated (i.e., a ubiquitin "tag" is added to the protein molecule), sulfated (i.e., a "sulfate group" is added to the protein molecule), or otherwise chemically modified.

Y. "Monomeric, dimeric and oligomeric proteins" shall mean correspond to single, dual or multiple joined peptide chains.

Z. "Inclusion" (or retractile) bodies shall mean dense, insoluble (i.e., not easily dissolved) protein aggregates (i.e., clumps) that are produced within the cells of certain microorganisms, generally by high expression levels of heterologous genes during fermentation. The term retractile bodies is used in some instances because their greater density (than the rest of the microorganism's body mass) causes light to be refracted (bent) when it is passed through them. This bending of light causes the appearance of very bright and dark areas around the retractile body and makes them visible under a microscope.

The term "retractile bodies" and "inclusion bodies" encompass insoluble cytoplasmic aggregates produced within a transfected host organism wherein the aggregates contain, at least in part, a heterologous protein to be recovered.

Excluded from the term inclusion bodies are aggregates of crystalline protein in Bacillus thuringiensis. While referred to as "inclusion bodies" in some of the literature, these are not inclusion bodies as the term is used herein but non-recombinant proteins in the range of 28–65 KDa, also called sporal or parasporal inclusion proteins, that are isolated from mosquito-specific *Bacillus thuringiensis.* (See, for example, Ishii and Ohba, Diversity of *Bacillus thuringiensis* environmental isolates showing larvicidal activity specific for mosquitoes. J. Gen. Microbiol. 139:2849–54, 1993; Ishii and Ohba, Investigation of mosquito-specific larvicidal activity of a soil isolate of *Bacillus thuringiensis* serovar canadensis. Curr. Microbiol. 35:40–3, 1997; and Wasano et al., delta-Endotoxin proteins associated with spherical parasporal inclusions of the four Lepidoptera-specific *Bacillus thuringiensis* strains. J. Appl. Microbiol. 84:501–8, 1998; and Yu et al., Characterization of mosquitocidal activity of *Bacillus thuringiensis* subsp. *fukuokaensis* crystal proteins. Appl. Environ. Microbiol. 57:1075–81, 1991).

Relatively rare in natural occurrence, refractile bodies can be induced (i.e., caused to occur) in procaryotes (e.g., bacteria) when the procaryotes are genetically engineered to produce eucaryotic (e.g., mammal) proteins. The proteins are stored in refractile bodies. For example, the *Escherichia coli* bacterium can be genetically engineered to produce bovine somatotropin (BST, a cow hormone) which is stored within refractile bodies in the bacterium. After some time of growth when a significant amount of BST has been synthesized the *Escherichia coli* cells are disrupted (i.e., broken open), and the refractile bodies are removed by centrifugation and washed. They are then dissolved in appropriate solutions to release the protein molecules. This step denatures (unfolds, inactivates) the BST molecules and they are refolded to their native state configuration (i.e., restored to the natural conformation found within the cow) in order to regain their natural activity. The protein is then formulated in such a way as to be commercially viable as a biopharmaceutical.

AA. "Activity-labile solubility form" refers to inclusion bodies containing insoluble proteins in a non-native state with altered tertiary structure that are subject to subsequent denaturation and inactivation upon solubilization by conventional methods. These are recovered in biologically active form by using the methods of solubilization described in embodiments of this invention.

BB. "Disrupting" the host organism (cell) shall mean the process of breaking the bacterial cells to isolate the inclusion bodies from the lysate containing cell debris and bacterial proteins by standard centrifugation and washing procedure steps.

CC. "Lysate" shall mean the residue from disruption of the host organism in the present method. A lysate arises, typically, from cytolysis, the dissolution of cells, particularly by destruction of their surface membranes. In some embodiments lysozyme lyse certain kinds of bacteria, by dissolving the polysaccharide components of the bacteria's cell wall. When that cell wall is weakened, the bacteria cell then bursts because osmotic pressure (inside that bacteria cell) is greater than the weakened cell wall can contain. In a particular embodiment of the present invention, cells are lysed by digestion with Lysozyme or disrupted by three cycles of cell dispersion with a Teflon homogenizer followed by centrifugation. In another embodiment, cells are disrupted by several passes in a pressurized homogenizer (e.g., Gaulin) or a microfluidizer.

DD. "Denaturant-free" shall mean the substantial absence of denaturant. Denaturant compounds include urea, guanidine, sodium thiocyanate, detergents and strong alkalis EE. "Solubilization solution" shall mean an acidic or alkaline aqueous solution, which is denaturant-free. Particular reference is made to strong chaotropic agents such as guanidinium chloride and sodium thiocyanate, Urea and strong detergents such as sodium dodecyl sulfate (SDS), which are not used in the processes of this invention. Instead, an effective concentration of $OH^-$ or $H^+$ ions and stabilizers such as a sugar (preferably Lactose) and a polyol (preferably Mannitol) in a non-buffered aqueous solution are used in this invention to induce solubilization of the protein aggregates. The $OH^-$ or $H^+$ ions and the stabilizers effectively interact with the side chains (sequence and properties) which determine all that is unique about the distinctive three-dimensional structure and biological activity of a particular protein. The correct conformation of the polypeptide chain thus results from the hydrogen, hydrophobic and charge interactions that occur in an aqueous solution containing $OH^-$ or H+ ions and the adjustment of various local and long-range constraints in the polypeptide chain during solubilization in the aqueous solution, yielding a biologically active protein. Constrains include the rigid planar nature of the peptide bond, the number and location of hydrophobic and hydrophilic residues in the sequence, the number and location of positive and negatively charged R groups, and the cysteine residues that form the disulfide bonds.

FF. "Chaotropic agent" refers to a compound that, in a suitable concentration in aqueous solution, is capable of changing the spatial configuration or conformation of proteins through alterations at the surface, rendering a protein to be isolated, soluble in the aqueous medium but without biological activity. Chaotropic agents are commonly used in combination with thiol compounds to cause S—S bond or disulfide bridge dissociation. Dissociation of these essential S—S bonds leads to loss of biological activity of proteins. Thiol compounds such as Beta-mercaptoethanol and Dithiotreitol (DTT) cleave disulfide bonds by reduction of S—S bonds to the —SH form of cysteine residues in the denatured protein. In reported methods employ such agents to refold recombinant polypeptide into a biologically active product, the denaturant must be removed from the denatured protein. In such methods it is required that SH groups are re-oxidized during refolding. This usually results in protein precipitation and low yields.

GG. "Stabilizing compounds" shall mean compounds such as sugars, polyols, amino acids and polymers, which in combination will increase the solubility and biological activity of a protein. The structure of a protein is strongly influenced by pH. Thus, in the presence of solutions containing low quantities of $OH^-$ or $H^+$ ions and stabilizers, ionization of the side chains occurs and solubilization takes place. Unfolding of tangled protein in inclusion bodies, at low concentration of the ions in the non-buffered aqueous solution, releases monomeric protein. Aqueous solutions containing osmolytic stabilizers such as sugars and polyols (polyhydric alcohols) provide protein stability, and thus the maintenance of solubility and biological activity of proteins. Such stability of protein structure by sugars is due to the preferential interaction of proteins with solvent components. The major effects of stabilizing compounds are on the viscosity and surface tension of the water. Many of these compounds include sugars, polyols, polysaccharides, neutral polymers, amino acids (glycine and alanine) and derivatives, and large dipolar molecules (i.e., trimethylamine N-oxide). Sugars such as Mannitol and Lactose maintain protein stability. Proteins are preferably hydrated in the presence of sugars. There is a positive change in the chemical potential of the protein induced by the addition of lactose and hence the stabilization of a protein. Polyols such as mannitol and glycerol are used also as protein stabilizers. Mannitol induces structure in the water molecules and stabilizes proteins by competing with water. This is believed due to the strong hydrophobic interaction between pairs of hydrophobic groups in the solutions of mannitol than in pure water. Without being bound by any specific theory, it is believed that Mannitol (and other polyols such as glycerol, sorbitol, arabitol and Xylitol) displace water allowing stabilization of hydrophobic interactions which are the major factor stabilizing the three-dimensional structure of proteins. Glycerol stabilizes proteins in solution, likely due to its ability to enter into and strengthen the water lattice structure. It is believed to prevent formation of precipitates by assisting preferential hydration and leads to the net stabilization of the native structure of proteins. Sorbitol likely competes for the hydration water of the protein stabilizing the protein from denaturation, and amino acids such as L-arginine, taurine, sarcosine, glycine and serine, likely increase the surface tension of water stabilizing proteins and suppressing aggregation. In some embodiments stabilizers include, but not limited to, sugars like lactose at about 5–12 mM or sucrose at about 2–10 mM; polyols like Mannitol at about 10–200 mM or glycerol at about 2–5%, and amino acids like methionine at about 10 mM in a buffered aqueous solution containing about 10 mM sodium phosphate or about 30–40 mM sodium bicarbonate at pH between about 8 and about 8.3, respectively.

HH. "Troponin" shall mean a complex of three subunits: Troponin I (TnI), which is believed to inhibit actomyosin; Troponin C (TnC), which is believed to remove TnI inhibition and Troponin T (TnT), which is believed to bind the Troponin complex to tropomyosin. Under one theory, upon Ca$^{2+}$ binding to TnC, the signal is transferred to the rest of the Troponin subunits and then to Tropomyosin. This leads to the interaction of myosin with actin and therefore muscle contraction. Troponin I is found in three isoforms: fast and slow twitch skeletal Troponin I and cardiac Troponin I. Human fast twitch skeletal Troponin I is the subunit of interest in this invention.

The present invention provides methods for solubilizing recombinant target peptides. In particular embodiments, target peptides are insoluble peptides associated with refractile or inclusion bodies produced by fermentation in transfected bacterial host cells. In one embodiment, inclusion body protein is precipitated or aggregated heterologous protein that is contained within prokaryotic host cells, or is otherwise prokaryotic host cell associated, and that assumes a conformation of altered (often reduced or eliminated) bioactivity.

It has now been discovered that solubilization solutions, solutions containing effective concentrations of OH$^-$ and H$^-$ ions, sugars or polyols, solubilize recombinant proteins sequestered in inclusion bodies while retaining native state configuration and or bioactivity. The invention further provides solutions and methods for stabilizing the solubilized recombinant proteins and maximizing biological activity of the proteins. In addition, the methods of the invention provide purification for proteins by solubilization and selective precipitation of contaminants in aqueous solutions, with particular reference to monomeric proteins.

Solubilization Solutions and Methods of the Invention

Solubilization of inclusion bodies is performed under a variety of conditions within the context of this invention. In particular embodiments, solubilization solutions contain effective concentrations of target protein which are, variously, alkaline or acidic solutions and both without the addition of salts. In a particular salt-free embodiment, inclusion bodies are solubilized and the solubilized proteins are thermodynamically stable and biologically active.

FIG. 1 presents a general schematic diagram of production of a biologically active recombinant protein from inclusion bodies expressed in *E. coli* by fermentation. In the schematic, prior to solubilization the inclusion bodies are isolated from bacteria by cell lysis with a Gaulin homogenizer followed by centrifugation and washing before solubilization.

In specific embodiments, the solubilization solutions contain one or more stabilizing compounds, such as sugars at about 2 to 12 mM or polyols at 10–200; sugar alcohol at about 2–5% and amino acids at about 10 mM, among other stabilizing compounds. The solubilization solution may include two or more stabilizing compounds selected from different chemical classes, such as one or more polyols and one or more sugars. Sugars may include sucrose, glucose, galactose, fructose, or mannose. Stabilizing polyols include sorbitol, glycerol, xylitol, or mannitol. Additional sugars and polyols suitable for use in solutions of the invention are listed in Back et al., "Increased thermal stability of proteins in the presence of sugars and polyols", *Biochemistry* 18:5191–6, (1979), and in Schein, "Solubility as a function of protein structure and solvent components", *Biotechnology* 8:308–17, (1990), both of which are herein incorporated by reference. As an example of a stabilizing amino acid, L-arginine may be added. Other stabilizing amino acids include taurine, sarcosine, glycine and serine, among others (see, for example, Arakawa and Timasheff, "The stabilization of proteins by osmolytes", *Biophys. J.* 47:411–4, (1985)).

The activity-labile solubility polypeptide to be solubilized is suspended in solubilization solution to produce a polypeptide preparation with approximately 1 to 10 mg polypeptide per ml solubilization solution. In a particular embodiment of the method, the polypeptide preparation has between about 2 and 5 mg polypeptide per ml solubilization solution. Alternatively, the solubilization preparation comprises between about 2.5 and about 3 mg polypeptide per ml solubilization solution. In another embodiment, about 2 g of washed, wet inclusion bodies are suspended in 100 ml solubilization solution. The inclusion body protein typically is solubilized more than 90% using the methods of the invention. In some embodiments, the insoluble polypeptide is solubilized at more than 95% or more than 99%.

Usefully, solubilization according to the invention occurs in the solubilization preparation as maintained at a temperature of about 10–30□ C. and preferably at a temperature of between about 22 and 25° C. In specific protocols, the solubilization solution is gently stirred during solubilization. Typically, the period over which solubilization occurs is about 20–30 minutes. The time necessary for solubilizing a particular preparation of inclusion bodies is dependent on a number of factors, including the overall charge of the protein, solubilization solution pH, solvent and solute composition of the solubilization solution, and temperature. Time for solubilization using solutions and methods of the invention is readily determined empirically for each different polypeptide. One empirical method is to look for the presence of particulates or cloudiness. Particulates or cloudiness are indicia of undissolved protein.

Polypeptides of the Invention

This invention is not limited to any specific type of peptides, polypeptides or proteins. Recombinant peptides, polypeptides or proteins useful in the invention are prepared by chemical sytheses or from biological systems including those employing a wide variety of heterologous genes or gene fragments to express the peptides, polypeptides or proteins.

While the compositions and methods of this invention are most useful for peptides or proteins which are found as inclusion bodies, other heterologous peptides or are to be understood as contemplated within this invention.

Attention is drawn to any peptide, polypeptide, or protein useful for human or veterinary therapy, diagnostic, screening, or research applications produced in insoluble form in any expression system. The methods and compositions disclosed herein are applied advantageously to hormones, cytokines, growth or inhibitory factors, enzymes, modified or wholly synthetic proteins or peptides, produced recombinantly in insoluble form in bacterial, yeast, mammalian or other eukaryotic cells and expression systems suitable therefor. Aspects of the invention are also applicable to the processing and formulating of polypeptides or proteins that are soluble when expressed or solubilized by conventional methods, such as with denaturants.

In one aspect, the methods can be applied to monomeric and fusion proteins, of sizes between about 10 and 100 kDa. Furthermore, the invention is tolerant of the level of hydrophobic amino acid residues, or the content of positively or negatively charged amino acid residues. The methods are particularly advantageous in the production of recombinant monomeric and fusion polypeptides containing from 1 to about 20 disulfide bonds. In one embodiment, the proteins of the invention are between about 16 and 60 kDa.

Recombinant Protein Production

Proteins for use in compositions and methods of the invention are conveniently expressed in transfected host cells from heterologous nucleic acid sequences that encode the proteins of interest. The nucleic acid sequences for transfection include any sequence that codes for a target polypeptide. Also contemplated are protein sequences synthetically constructed from the amino acids individually or in peptide units, or sequences of native coding within a cell that normally expresses a given polypeptide. Further contemplated are nucleotide sequences which have been modified. Attention is drawn to Sambrook et al., 1990, *Molecular Cloning, A Laboratory Manual,* 2d ed., Cold Spring Harbor Laboratory, Cold Spring Harbor, N.Y. Sequence modifications are usefully introduced to vary expression control elements, to produce desired changes in amino acid composition of the expressed protein, to modify expression levels, or to produce fusion proteins.

DNA sequences encoding polypeptides of the invention are be expressed in vivo in either prokaryotes or eukaryotes and elsewhere. A particular host expression system is chosen depending on the characteristics and intended use of the target polypeptide, and economic factors associated with each host expression system. Some proteins of pharmacologic interest, such as glycoproteins, are normally produced in vivo with specific patterns of posttranslational glycosylation. Normal glycosylation may be required if the recombinantly produced protein is to exhibit bioactivity or acceptable pharmacokinetic or therapeutic properties. Production of proteins with native state configuration, here in reference to glycosylation patterns, typically requires either production in expression systems with extensive subsequent modification, or production in a eukaryotic host cell, such as a CHO cell strain or another mammalian host cell type. Hosts organisms include fungi, yeast, baculovirus/insect, and mammalian cell based systems. *Eschericia coli, Bacillus subtilis, Pseudomonas,* and other bacteria are also employed in this method. *E. coli* constitutes a particularly useful type of host cell for recombinant protein production. Useful yeast include species of *Streptomyces, Saccharomyces cerevisiae, Saccharopolyspora,* and *Aspergillus.* A number of strains of eukaryotic cells are known to those skilled in the art which are useful as host cells for expression of the peptides, polypeptides, and proteins of the present invention.

Transformation of a host organism with recombinant DNA is usefully accomplished by conventional techniques well known to those skilled in the art. Where the host organism is prokaryotic, such as *E. coli,* competent cells which are capable of DNA uptake can be prepared from cells harvested after exponential growth and subsequently treated by the $CaCl_2$ method using procedures well known in the art. Alternatively, $MgCl_2$ or RbCl could be used.

Where the host organism is a eukaryote, various methods of DNA transfer are used. These include transfection of DNA by calcium phosphate precipitates, conventional mechanical procedures such as microinjection, insertion of a plasmid encased in liposomes, electroporation or the use of viral vectors. DNA are expressed in yeast by inserting the DNA into appropriate expression vectors and introducing the product into the host organism.

Transfected host organisms are grown under conditions permissive for protein expression. Induction includes temperature modulation or addition of IPTG. In cellular expression systems, cells are conveniently harvested by centrifugation. Fermentation is carried out under conditions of sufficient time, temperature, and pH, to result in the formation of inclusion bodies comprising the recombinant protein within host cells.

Target peptide bearing cells are disrupted by any of numerous methods, including by lysis using suitable reagents and buffers, by double passage through an homoginizer such as a Manton Gaulin® homogenizer (Gaulin Corp., Everett Mass., USA), or by use of multiple passes on through a microfluidizer such as the Microfluidizer® (Microfluidics Corp., Newton Mass., USA) set for highest pressure. In addition, sonication and use of a French press, either alone or in combination with low levels of detergents is useful.

Inclusion bodies and other insoluble components in the cell lysate are pelleted by low-speed centrifugation, washed, and solubilized according to the solubilization methods of the invention, described in detail elsewhere in this disclosure.

Protein Purification

Embodiments of the invention include purification steps incorporating differential precipitation of target and contaminant polypeptides and host cell components. One method for purifying recombinant proteins uses a non-buffered acidic solution including at least one stabilizing compound, and HCl between about 10 and about 20 mM. A protein solution is produced by adding to the non-buffered solution a recombinant polypeptide between about 1 and about 4 mg polypeptide per ml non-buffered solution, wherein the protein solution has a pH of between about 2.0 and about 3.0, in one embodiment between about pH 2.2 and 2.6. The solution may be centrifuged or filtered to separate out contaminant proteins, including many host cell proteins. Dialysis is also useful as well as ultrafiltration or diafiltration. The supernatant contains the target peptide in solution. The pH of the supernatant is then increased to between about 4 and 5 using 1N NaOH. In one embodiment, the pH for this step is about pH 4.6. This pH increase precipitates additional contaminant proteins, which are removed by centrifugation. The precipitate-free supernatant is recovered and the pH of the supernatant may then be adjusted to between about pH 9 and 10.5 with 1N NaOH.

Protein is usefully further isolated using a non-buffered alkaline solution including a stabilizing compound and NaOH between about 8 and about 10 mM. This results in a protein solution by adding between about 1 and about 4 mg recombinant polypeptide per ml non-buffered solution, yielding protein solution with a pH of between about 9 and about 11.2. The pH of the protein solution is then lowered to between about 4 and 5 using 1N NaOH, the solution is centrifuged or filtered, and the precipitate-free supernatant is recovered. The pH of the supernatant may be adjusted to between about pH 9 and 10.5 with 1N NaOH.

Use of Solutions of the Invention with Processes Utilizing Chaotropic Agent or Detergents Target peptides that have been solubilized at high concentrations with chaotropic reagents such as 8 M urea or 6 M guanidine hydrochloride are renatured or stabilized at high protein concentrations with retained solubility and bioactivity after partial or total removal of chaotrope by using a stabilization buffer containing a salt and stabilizers. In the presence of stabilization buffer the proteins are believed to oxidize and refold into bioactive form. Folding is accomplished when the amino acid sequence of the protein is free to interact and assume its native secondary and tertiary structure.

In some embodiments it is useful to employ reducing agents, such as dithiothreitol (DTT) in the stabilization buffer to maintain bioactivity. In addition protein aggregation, precipitation and accumulation of inactive species are minimized. The concentration of chaotropic agent in the chaotrope-containing polypeptide solution is reduced by dialysis, without further dilution of the solution, against a stabilizer-containing renaturing buffer of pH between about 9 and about 11.2 and buffer concentration between about 10 and about 50 mM. In one embodiment, the buffer is ethanolamine between about 20 and 30 mM, pH 10.3, containing a polyol (e.g. glycerol, 5–10%) and a sugar (e.g. lactose, 5–10 mM).

Resultant target polypeptide is conveniently purified chromatographically, and then dialyzed against an aqueous stabilization buffer containing one or more stabilizing compounds. In a particular embodiment, the stabilizing compound is a sugar or a polyol at between about 5 and 100 mM. In another embodiment, the stabilizing compound makes up between about 2 and about 15% of the total stabilization buffer. This procedure reduces protein aggregation and precipitation.

Stabilizing and Formulating Proteins

The invention also provides a method for formulating recombinant polypeptide, including dialyzing (for example, for between about 24 and 48 hours) or ultrafiltering the polypeptide into an aqueous stabilization buffer including a stabilizing compound, and sterilizing the dialyzed or filtrated recombinant polypeptide by filtration. The stabilization buffer may include protein concentrations of between about 2 and 10 mg per ml solution, as well as buffer salt at concentration between about 5 and 40 mM. In one embodiment, the stabilizing compound in the stabilization buffer is between about 5 and 100 mM. In another embodiment, the stabilizing compound makes up between about 2 and about 10% of the total stabilization buffer. Another embodiment of a stabilization buffer may include 30 to 40 mM sodium bicarbonate pH 8.0, or 10 to 20 mM sodium phosphate pH 8.0. The buffer may contain any or all of the following: between about 5 and 10 mM lactose or sucrose; 10 to 100 mM mannitol; 2% to 5% glycerol; and 10 mM methionine or cysteine. In some embodiments, a salt such as NaCL may be added to the final product to adjust the osmolality of the final product (isolated protein preparation) to physiological levels.

For storage, a sterilized protein may be dispensed into sterile glass vials. In particular instances, proteins are be stored at about −20☐ C. or at colder temperatures, such as about −80☐ C. or below. Particular reference is made to storage containers held in liquid nitrogen.

Pharmaceutical Compositions

The invention provides for pharmaceutical compositions containing proteins of the invention. Formulations for these compositions may include any formulation in which the compounds of the invention are suitable for their therapeutic purpose, and which conform to medical and regulatory standards for safety and efficacy. The compositions of the invention may be applied in a pharmaceutically acceptable preparation, meaning a preparation which produces medically desirable therapeutic effects without concurrently causing clinically significant adverse effects. Clinically significant side effects refer to unacceptable side effects of the preparation, including either medically or cosmetically unacceptable effects. The compounds of the invention are administered in therapeutically effective amounts. A therapeutically effective amount is one which causes medically desirable effects. It should be understood that although specific formulations have been defined, many variations are possible. Dosage levels will vary greatly depending upon the individual to be treated and the specific medicament used. Proper dosing can be determined without undue experimentation and according to procedures well known to those of ordinary skill in the art.

In addition, the invention includes a method of producing reactive antibodies by immunizing a vertebrate animal with proteins produced, refolded or isolated using the methods taught herein.

EXAMPLE 1

Target Peptide Solubilization in Alkaline Solution

Broadly, this method includes (i) propagating host cells genetically engineered to elaborate a target peptide (ii) disrupting the host cell to produce a lysate, (iii) precipitating the target peptide from the lysate, and (iv) recovering lysate precipitate containing the polypeptide. In this embodiment, the lysate precipitate is resuspended in an alkaline denaturant-free, non-buffered solubilization solution to produce a solubilization preparation containing a concentration of polypeptide between about 1 and about 4 mg polypeptide per ml solubilization solution.

The amount of polypeptide dissolved per ml of solubilization solution is empirically determined for each particular protein by solubilizing different amounts of the aggregates in a constant volume of solubilization solution.

In this example, the solubilization solution contains NaOH at between about 8 and 10 mM, and has a pH between about 10.5 and about 11.2. The solubilization solution further contains stabilizers such as a polyol (such as mannitol between about 2.0 and 10 mM) and a sugar (such as lactose between about 1.0 and 5 mM) to stabilize the protein's exposed polar groups and hydrophobic residues. In one typical example, the alkaline solubilization solution contains 9 mM NaOH and initially has pH of about 11.2. The inclusion bodies are solubilized by stirring gently at room temperature (between about 20° C. and about 25° C.) between about 20 to 40 minutes, and particularly for about 30 minutes. After 20–30 min of stirring at room temperature, the pH of the preparation drops to pH between about 9.5 to 10.2 as the protein solubilizes and interacts with the OH ions and stabilizers in the aqueous solution. The preparation is then centrifuged for about 15 minutes at 20,000 rpm at 4° C. to remove insoluble material. The supernatant fluid provides an supernatant of the target peptide with a final pH of between about 9.5 to 10.3. The supernatant is maintained for several hours to overnight at room temperature, without disruption, to increase the yield of monomeric protein. The protein concentration is at this point typically between about 2 and mg/ml, depending of the polypeptide. Optionally, the method includes subsequently adjusting the pH of the raw protein extract with diluted acid or base.

Adjustment of pH depends on the isoelectric point (pI) of a particular protein and of the first purification step (anion vs. cation exchange chromatography). The pH of the preparation is usefully at least about one unit pH different from (above or below) the pI to achieve proper binding of the protein onto the chromatographic media.

EXAMPLE 2

Solubilization in Acidic Solution

Recombinant polypeptides are solubilized at low pH from inclusion bodies. An aqueous solution is prepared containing sufficient H⁻ ions in the form of HCl to solubilize the protein. Typically, the concentration of HCl is between about 10 and 20 mM and has pH between about 2.2 and 2.8. The solution, the acidic solubilization solution', optionally contains stabilizers such as a polyol (e.g. glycerol between about 2.0% and 5.0% or mannitol between about 2 mM and 3 mM) or a sugar, such as lactose between about 1.0 and 2.5 mM to stabilize the exposed polar groups and hydrophobic residues in the target peptides.

As with alkaline solutions, this method includes (i) propagating host cells genetically engineered to elaborate a target peptide (ii) disrupting the host cell to produce a lysate, (iii) precipitating the target peptide from the lysate, and (iv) recovering lysate precipitate containing the polypeptide. Resuspension of the lysate precipitate is performed with about 1.8 to 2.0 g wet-weight of inclusion bodies per 100 ml of solubilization buffer. The resuspended solution is stirred gently at room temperature (22° C. to 25° C.) for about 1 to 3 hours, and, in a typical example, for about 2 hours. The preparation is centrifuged for about 15 minutes at 20,000 rpm at 4° C. to remove insoluble material. A supernatant containing the target peptide is obtained with a final pH of between about 2.5 and 2.8. The pH of the protein supernatant is adjusted from acidic to a pH of about 9.5 with NaOH. The protein supernatant is maintained for several hours to overnight at room temperature without disruption to increase the yield of monomeric protein. The supernatant containing the target peptide is purified according to established methods. The protein concentration is at this point typically between about 2 and 5 mg/ml. The next step is stabilizing the solubilized recombinant polypeptide in an aqueous solution containing a buffered salt and stabilizers.

EXAMPLE 3
Stabilization of Protein Solutions

Purification of recombinant troponin in native state configuration with bioactivity is illustrative of the process of this invention. Solubilized recombinant troponin is stabilized in an aqueous solubilization solution containing a buffered salt and stabilizers. This method includes preparing a stabilization buffer containing a buffered salt, such as sodium bicarbonate between about 30 and 40 mM, pH 8.0, or sodium phosphate between about 10 and 30 mM. The stabilization buffer also contains one or more stabilizers, which include a sugar (e.g. lactose) between about 5 and 12 mM, or a polyol (e.g. mannitol at about 10–100 mM or glycerol between about 2% and about 10%) and sodium chloride at a final concentration of 0.1M to raise the osmolality of the preparation to physiological levels. The solubilized recombinant polypeptide is dialyzed against or ultrafiltered in the stabilization buffer. The dialyzed or ultrafiltered recombinant polypeptide is sterilized by filtration, and dispensed into sterile glass vials.

EXAMPLE 4
Purifying Proteins Solubilized in Acidic Solution

Removal of contaminant proteins from preparation of target peptide solubilized in an acidic solubilization solution is accomplished by the following method. Isolated inclusion bodies containing the target peptide are solubilized in an aqueous solution of acid pH containing stabilizers. The pH of the solubilization solution containing the dissolved target peptide is increased at least 1.5 pH units using 1N NaOH, to obtain a pH between about 4.2 to 4.8, and in one example between about pH 4.6 and 4.7. The supernatant is centrifuged to remove precipitated proteins at 15,000 rpm and 4° C. for 15 minutes. The pH of the supernatant is adjusted to about 9.8 with 1N NaOH, and the protein maintained for several hours to overnight at room temperature to increase the yield of monomeric protein. The supernatant is dialyzed into stabilization buffer for at least 24 h at about 22° C. to 25° C., or alternatively subjected to ultrafiltration and diafiltration in stabilization buffer. The target peptide is further purified using any appropriate chromatographic procedure, and dialyzed against stabilization buffer.

EXAMPLE 5
Purifying Proteins Solubilized in Alkaline Solution

This method exemplifies the removal of contaminant proteins and production of highly isolated monomeric recombinant target peptides from solution of target peptides solubilized under alkaline conditions. Inclusion bodies containing target peptides are solubilized in an alakaline aqueous solubilization solution containing stabilizers. The pH of the alkaline solubilization solution containing the proteins is then decreased by addition of HCl or another acid to pH between about 4.2 and 4.8, and in one example between about pH 4.6 and 4.7. The solubilization solution is centrifuged to remove precipitated proteins at 15,000 rpm and 4° C. for 15 minutes. The pH of the supernatant is adjusted to about pH 9.8 with 1N NaOH, and maintained for several hours to overnight at room temperature to increase the yield of monomeric protein. The protein solution is dialyzed against stabilization buffer for about 24 h or longer at about 22° C. to 25° C., or alternatively, the target peptide in solution is formulated in stabilization buffer by ultrafiltration and diafiltration yielding purified target peptide.

EXAMPLE 6
Solubilization of Target Peptide Inclusion Bodies at Elevated pH

Fish somatrotopin is expressed in *E. coli* transformed with plasmid pRE-1-CSGH containing a heterologous nucleotide sequence that codes for Coho salmon (*Oncorhynchus kisutch*) growth hormone. These *E. coli* host cells are grown in LB medium containing antibiotic (Amp-50 ug/ml) and 20% glycerol and induced by increasing the temperature of the culture from 30° C. to 37° C. for 2 hours.

Host cells are lysed in 20 mM Tris/Cl pH 8.0, 20% sucrose, 1 mM EDTA stirring 1 hour at room temperature. The lysate is strained through 2 layers of cheesecloth to remove cell debris and centrifuged for 20 minutes at 10,000 rpm. The pellet containing the inclusion bodies is resuspended in 50 mM Tris/Cl pH 8.0, 0.5 mM phenymethylsulfonyl fluoride (PMSF) and 5 mM EDTA.

The resuspended lysate is sonicated three times (50W) each with a 3 -sec pulse. lysozyme (200 ug/ml) and DNAse 1 (20 ug/ml) are added. The resuspended lysate is incubated at 4° C. with gently stirring overnight. This step reduces the viscosity of the supernatant and removes nucleic acids. The inclusion bodies are recovered by centrifugation at 15,000 rpm at 4° C. for 20 minutes, and washed in 50 mM Tris/Cl pH 8.0, 5 mM EDTA, and 1% Triton-X-100, stirred for 1 hour at room temperature and centrifuged for 15 minutes at 15,000 rpm at 4° C. This step is repeated two more times. The inclusion body pellet is then resuspended in 20 mM Tris/Cl pH 8.0 and 5 mM EDTA, stirred for 1 hour at room temperature and centrifuged for 15 minutes at 15,000 rpm at 4° C. This step is repeated two more times. The inclusion body pellet is then resuspended in dH$_2$O, stirred for 1 hour at room temperature and centrifuged for 20 min at 15,000 rpm at 4° C. This step is repeated two more times. The final pellet containing the inclusion bodies is immediately solubilized in solubilization buffer containing 2 mM lactose, 2.5 mM mannitol and 10 mM NaOH with a final pH ~11.0 by gently stirring for 30 minutes at room temperature. After solubilization, the target peptide from the inclusion bodies, fish somatotropin, is subjected to purification onto a Sepharose® CL-6B column equilibrated with 10 mM ammonium bicarbonate pH 10.0. Fractions containing fish somatotropin are pooled and dialyzed 48 h against a stabilization buffer containing 40 mM sodium bicarbonate, 20 mM mannitol, 6 mM lactose and 10 mM methionine with a final pH of about 8.0, with a buffer change after 24 h. The fish somatotropin is filter-sterilized, dispensed in small glass vials, sealed, lyophilized and stored dried at 4° C.

Alternatively, the pH of the solubilized protein is adjusted to 9.5 and the fish somatotropin is maintained for several hours to overnight at room temperature without disturbing to increase the yield of monomeric protein before purification.

The biological activity of the fish somatotropin, csGH, was determined by assessing the growth promoting activity of the hormone in the fish Carassius auratus that were acclimated for two weeks in glass tanks with aerated water at about 12° C. The fish were fed twice a day to satiation with dry fish food (commercial trout pellets). Fish were injected intraperitoneally with recombinant csGH diluted with PBS at 5–8 ug/g body weight per week over a 6 week period. The weight gain in fish receiving the isolated fish somatotropin was about 1.5 to 1.7 as compared with untreated or saline injected control fish establishing the bioactivity of the fish somatotropin isolated by the instant method.

EXAMPLE 7
Isolation of Monomeric Somatotropin

Fish somatotropin is expressed in the host cell, E. coli transformed with plasmid pRE-1-CSGH containing a heterologous nucleotide sequence that codes for Coho salmon growth hormone. The E. coli cells are grown under the conditions described in Example 6 and the inclusion bodies are isolated and purified also as described in Example 6. The final pellet containing the inclusion bodies is solubilized in the solubilization solution as described in Example 6. The pH of the solubilization solution containing the target peptide, fish somatotropin, is then adjusted to pH 9.5. This solution is maintained for several hours to overnight at room temperature without disturbing to increase the yield of monomeric protein. The solution is dialyzed or directly transferred to deionized water containing 100 mM mannitol and stored overnight at 4° C. without disturbing. Fish somatotropin as a monomeric protein is isolated from the solution on a Sephacryl® –100 column equilibrated with 6.5 mM borate buffer pH 10.0. The isolated protein is dialyzed in 'stabilization buffer' containing 40 mM sodium bicarbonate pH 8.0, 50 mM mannitol, 12 mM lactose and 10 mM methionine. The fish somatotropin is processed and stored as described in example 6.

EXAMPLE 8
Solubilization of Inclusion Bodies at Low pH

Fish somatotropin is expressed in the host cell E. coli transformed with plasmid pRE-1-CSGH containing a heterologous nucleotide sequence that codes for Coho salmon growth hormone. The E. coli cells are grown under the conditions described in Example 6 and the inclusion bodies are isolated and purified also as described in Example 6. The final pellet containing the inclusion bodies is solubilized in an aqueous solution containing 10 to 20 mM HCl pH about 2.2, 1% glycerol and 2 mM lactose by gently stirring at room temperature for about 2.0 hours. Insoluble proteins, including most E. coli proteins, are removed by centrifugation. The solubilized protein is adjusted to pH 9.5 to 10.0 with 1N NaOH and is maintained for several hours to overnight at room temperature without disturbing to increase the yield of monomeric protein. The protein is then purified as described in Example 7. The pooled fractions containing isolated fish somatotropin are dialyzed against the stabilization buffer containing 30 mM sodium bicarbonate, 10 mM methionine, 5 mM lactose and 10 mM mannitol, pH 8.0. The fish somatotropin is processed and stored as described in Example 6, and the bioactivity of the recombinant hormone is assessed as described in Example 6.

EXAMPLE 9
Removal of Contaminant Proteins by Solubilization of Inclusion Bodies at Low pH and Recovery of Monomeric Somatotropin Fish somatotropin is expressed in a host cell E. coli transformed with plasmid pRE-1-CSGH containing a heterologous nucleotide sequence that codes for Coho salmon (Oncorhynchus kisutch) growth hormone. The E. coli cells are grown under the conditions described in Example 6 and the inclusion bodies are isolated and purified also as described in Example 6. To isolate fish somatotropin the inclusion bodies are solubilized in an aqueous solution of low pH according to the procedure described in Example 8, followed by increasing the pH of the solution to a pH of about 4.6 to about 4.7. This increase in about two pH units precipitates contaminant proteins, which are removed by centrifugation. The pH of the solution is then increased to pH 9.5 with 1N NaOH and is maintained for several hours to overnight at room temperature without disturbing to increase the yield of monomeric protein. The monomeric protein fish somatotropin is transferred into the stabilization buffer according to the procedure described in Example 6.

EXAMPLE 10
Removal of Contaminant Proteins by Solubilization of Inclusion Bodies at Elevated pH and Recovery of Monomeric Somatotropin To isolate fish somatotropin from inclusion bodies, the inclusion bodies containing fish somatotropin are solubilized in an aqueous solution according to the procedure described in Example 6, followed by lowering the pH of the solution to an acidic pH between about 4.6 and about 4.7. This drop in pH precipitates contaminant proteins, which are removed by centrifugation. The pH of the solution is then increased to pH 9.5 with 1N NaOH and is maintained for several hours to overnight at room temperature without disturbing to increase the yield of fish somatotropin. The fish somatotropin is transferred into the stabilization buffer according to the procedure described in Example 6.

EXAMPLE 11
Stabilization of Denatured Somatotropin

Fish somatotropin is expressed in the host cell E. coli transformed with plasmid pRE-1-CSGH containing a heterologous nucleotide sequence that codes for Coho salmon growth hormone. The E. coli cells are grown under the conditions described in Example 6 and the inclusion bodies are isolated and purified also as described in Example 6. The final pellet containing the inclusion bodies is immediately solubilized in 20 mM ethanolamine pH 10.3 containing 8 M urea and 0.15 M NaCl for 30 minutes with gently stirring at room temperature. The solubilized protein is then dialyzed to remove urea and salt for 48 hours with a change of buffer after 24 hours at room temperature in 40 mM sodium bicarbonate pH 8.0 containing 100 mM mannitol and 10 mM lactose at a protein concentration between about 2–5 mg/ml. After dialysis the recombinant protein is purified by a two-step chromatography that includes CL-6B SEPHAROSE® (4% cross-linked agarose and SEPHACRYL-100® (dextran/bisacrylamide matrix. Fractions containing fish somatotropin are pooled and dialyzed against stabilization buffer described in Example 8. The bioactivity of the fish somatotropin is assessed as described in Example 6.

EXAMPLE 12

Fish somatotropin is expressed in a host cell E. coli transformed with plas mid pAF51 containing a heterologous nucleotide sequence that codes for rainbow trout (Oncorhynchus mykiss) growth hormone, the target peptide. The E. coli cells are grown in TB medium containing antibiotic (Amp-50 ug/ml) and 20% glycerol, and induced by adding 0.4 mM IPTG at 37° C. for 3 hours. The inclusion bodies are isolated from the cells with 50 mM Tris/Cl pH 8.5, 20% sucrose, 1 mM EDTA by stirring 1 hour at room temperature (room temperature). The solubilization solution containing the target peptide is strained through 2 layers of cheesecloth to remove cell debris and centrifuged for 20 minutes at 15,000 rpm. The pellet containing the inclusion bodies is resuspended in 500 ml of 50 mM Tris/Cl pH 8.0, 40 mM EDTA, 8% sucrose, 5% Triton-X-100, lysozyme (100 ug/ml) and DNAse 1 (20 ug/g of bacteria cells) at 4° C. This step reduces the viscosity of the supernatant and removes DNA. The inclusion bodies are washed overnight by stirring. After centrifugation at 15,000 rpm at 4° C. for 20 minutes the inclusion bodies are washed in 50 mM Tris/Cl pH 8.0, 20 mM EDTA, 1% Triton-X-100 for 2 hours at room temperature and the inclusion bodies pelleted by centrifugation 20 minutes at 15,000 rpm at 4° C. This step is repeated twice. The inclusion body pellet is resuspended in 20 mM Tris/Cl pH 8.0, 5 mM EDTA, stirred for 1 hour at room temperature and centrifuged for 20 minutes at 20,000 rpm at 4° C. This step is repeated twice. The inclusion body pellet is resuspended in $dH_2O$, stirred for 1 hour at room temperature and centrifuged for 20 min at 20,000 rpm at 4° C. This step is repeated twice. The inclusion body pellet is stored at −20° C. or immediately solubilized in a solution containing 2 mM lactose, 2% glycerol and 10 mM NaOH with a final pH of about 11.2 for 30 minutes at room temperature. After solubilization the target peptide is maintained for several hours to overnight at room temperature without disturbing to increase the yield of monomeric target peptide. The target peptide is isolated by anion and cation exchange chromatography. The fractions containing somatotropin are dialyzed 48 hs against 10 mM phosphate buffer solution, pH 8.0 containing 10 mM methionine, 12 mM mannitol and 6 mM lactose with a buffer change after 24 h. The bioactivity of recombinant rtGH is determined by assessing the growth promoting activity of the hormone in the fish Carassius auratus as presented in Example 6.

EXAMPLE 13

Fish somatotropin is expressed in host cell *E. coli* transformed with plasmid pGEM-3Z-sbGH containing a heterologous nucleotide sequence that codes for striped bass (*Morone saxatilis*) growth hormone (sbGH). The *E. coli* cells are grown in LB medium with antibiotic at 30° C. and induced by increasing the temperature of the culture to 42° C. for 2 hours. The inclusion bodies are isolated from the bacterial cells with 50 mM Tris/Cl pH 8.0, 10 mM EDTA, 1 mM PMSF, and 2 mg/ml lysozyme; after sonication (three bursts of 5 sec-pulse each) the pellet is collected by centrifugation at 12,000 rpm for 30 minutes at 4° C.

The inclusion body pellet is then washed three times with 10 mM EDTA and 1% Triton-X-100, and twice with 1.5 mM GuHCl. Detergent and chaotropic reagent are removed by washing the pellet three times with $dH_2O$ with gently stirring for 1 hour at room temperature. The inclusion bodies are recovered by centrifugation at 20,000 rpm for 20 minutes at 4° C. and stored at −20° C. or solubilized in the solubilization solution containing 2.5 mM mannitol, 1.0 mM lactose, and 10 mM NaOH. The solubilized recombinant protein is maintained for several hours to overnight at room temperature without disturbing to increase the yield of monomeric protein and then it is purified by a two step anion exchange chromatography. Fractions containing somatotropin are dialyzed against a stabilization buffer containing 40 mM sodium bicarbonate pH 8.0, 12 mM mannitol and 6 mM lactose and 10 mM methionine.

The bioactivity of the resulting somatotropin is determined by a radioreceptor competition-binding assay and by induction of hepatic insulin-like growth factor 1 (IGF-1) mRNA synthesis in vivo. Briefly, striped bass microsomes from striped bass hepatic tissue are mixed with $^{125}$I-labeled native tilapia GH in 20 mM Tris/Cl pH 7.0 with 10 mM $MgCl_2$, 0.5% BSA and 0.1% $NaN_3$ and incubated with 1 ug of tGH for 18 h at 15° C. The reaction is terminated by adding cold assay buffer followed by centrifugation at 10,000 g for 20 minutes. Radioactivity of the resulting pellet by a gamma counter is used to determine the ability of recombinant sbGH to displace radiolabeled native tilapia GH. Displacement curves show a 50% displacement value for sbGH, which is about 20-fold that of native tilapia GH. This value shows an appreciable sbGH binding. The effect of recombinant sbGH on the stimulation of hepatic IGF-1 gene expression in vivo is determined by injecting various doses of the hormone into rainbow trout and measuring the level of the hepatic IGF-1 mRNA by RNAse protection assay.

At a dose of 1 ug/g of body weight a 7-fold increase in hepatic IGF-1 mRNA level is observed when compared to that in control fish. The results of both assays establish that the recombinant sbGH is bioactive.

EXAMPLE 14

Fish prolactin is expressed in host cell *E. coli* transformed with plasmid pRE-1-rtPRL containing a heterologous nucleotide sequence that codes for rainbow trout (*Oncorhynchus mykiss*) prolactin (rtPRL). The *E. coli* cells are grown in LB medium containing ampicillin (50 ug/ml) and 20% glycerol and induced by increasing the temperature of the culture from 30° C. to 42° C. for 2 hours. The cells are lysed in 20 mM Tris/Cl pH 8.0, 20% sucrose, 1 mM EDTA stirring 1 hour at room temperature (room temperature). The solubilization solution containing the inclusion bodies is centrifuged for 20 minutes at 10,000 rpm. The pellet containing the inclusion bodies is resuspended in 50 mM Tris/Cl pH 8.0, 0.5 mM PMSF and 5 mM EDTA and lysozyme (200 ug/ml) and DNAse 1 (20 ug/ml) are added to reduce viscosity and remove nucleic acids (DNA).

The inclusion bodies are recovered by centrifugation at 15,000 rpm at 4° C. for 20 minutes and are washed in 50 mM Tris/Cl pH 8.0, 5 mM EDTA, and 1% Triton-X-100, stirred for 1 hour at room temperature and centrifuged for 15 minutes at 15,000 rpm at 4° C. This step is repeated two more times. The pellet is then resuspended in 20 mM Tris/Cl pH 8.0 and 5 mM EDTA, stirred for 1 hour at room temperature and centrifuged for 15 minutes at 15,000 rpm at 4° C. This step is repeated two more times. The pellet is then resuspended in $dH_2O$, stirred for 1 hour at room temperature and centrifuged for 20 min at 15,000 rpm at 4° C. This step is repeated two more times. The final pellet containing the inclusion bodies are stored at −20° C. or immediately solubilized in the solubilization buffer containing 2 mM lactose, 5% glycerol and 9 mM NaOH with a final pH ~11.0 by gently stirring for 30 minutes at room temperature.

After solubilization, fish prolactin is maintained for several hours to overnight at room temperature without disturbing to increase the yield of monomeric protein followed by purification. Fractions containing prolactin are pooled and dialyzed for 48 h with a buffer change after 24 h against a stabilization buffer containing 40 mM sodium bicarbonate, 12 mM mannitol, 6 mM lactose and 10 mM methionine with a final pH of about 8.3. The cross-reactivity of recombinant rtPRL with fish PRL antiserum is assessed. The resulting prolactin is established to be bioactive and fully cross-reactive.

EXAMPLE 15
Solubilization of Inclusion Bodies at Elevated pH

Recombinant troponin I, the target peptide, is expressed in host cell *E. coli* transformed with plasmid BLS-1 containing the full length of human fast twitch skeletal muscle troponin I.

The *E. coli* cells are grown in culture medium containing LB plus Kanamycin at 37° C. and induced by adding 0.5 mM IPTG to the culture to reach an $OD_{600nm}$ of 6.0. The bacterial cells are dispersed with a Teflon homogenizer in 50 mM sodium acetate, 2 mM EDTA, 0.5 M sodium chloride, 1% Triton-X-100 pH 6.0 and pelleted by centrifugation at 4° C. at 8750 rpm for 30 minutes. The pellet is again dispersed with a Teflon homogenizer in 50 mM sodium acetate, 2 mM EDTA and 0.5 M sodium chloride, pH 6.0 and pelleted by centrifugation at 4° C. at 8750 rpm for 30 minutes. The pellet is then dispersed with a Teflon homogenizer in 50 mM sodium acetate and 2 mM EDTA pH 6.0 and pelleted by centrifugation at 4° C. at 6000 rpm for 30 minutes. The inclusion bodies are solubilized in solubilization buffer containing 2.0 mM mannitol, 1.0 mM lactose and 9 mM NaOH with gently stirring at room temperature for 30 minutes. The supernatant is centrifuged for 15 minutes at 20,000 rpm at 4° C. to remove insoluble material. The supernatant is maintained for several hours to overnight at room temperature without disturbing to increase the yield of monomeric protein.

Troponin I is then purified by a three step process that include anion exchange chromatography on a quaternary ammonium ion-exchange column (Q-SEPHAROSE® (dextran cross-linked agarose), Amersham Pharmacia Biotech), hydrophobic interaction chromatography on PHENYL SEPHAROSE® (phenyl- cross-linked agarose) (Amersham Pharmacia Biotech) and a second anion exchange chromatography on Q-SEPHAROSE® (dextran cross-linked agarose). Fractions containing troponin are dialyzed against a stabilization buffer containing 30 mM sodium bicarbonate pH 8.0, 10 mM mannitol and 5 mM and sodium chloride to raise the osmolality of the preparation to physiological levels. The dialyzed supernatant is filter-sterilized, dispensed in sterile vials and stored at −20° C. The potency of recombinant troponin I is assessed in vitro by inhibiting cell growth in the presence of basic fibroblast growth factor. Briefly, capillary endothelial cells (EC) are plated on gelatinized 96-well culture plates in DMEM media supplemented with 5% calf serum and incubated for 24 hours. On day 2 cells are treated with basic fibroblast growth factor (bFGF-1 ng/ml) and challenged with purified recombinant troponin I that is diluted in PBS ($Na_2HPO_4$ 5 mM, $KH_2PO_4$ 1.5 mM, NaCl 0.15M). Control cells contain cells alone or cells stimulated with bFGF. On day 5 growth medium is removed from the plates and cells are lysed in buffer containing Triton-X-100 and the phosphatase substrate p-nitrophenil phosphate. After incubation for 2 h at 37° C., NaOH is added to terminate the reaction and color development is monitored on a standard plate reader. Biologically active purified rTN-I inhibits bFGF-stimulated capillary EC. Inhibition of EC proliferation is carried out in a dose-dependent and saturable manner when bFGF is used as the mitogen. The presence of bioactive Troponin I is established.

EXAMPLE 16
Solubilization of Inclusion Bodies at Low pH and Removal of Contaminant Proteins Recombinant troponin I is expressed in host cell *E. coli* transfected with plasmid BLS-1 containing the full length of human fast twitch skeletal muscle troponin I. The *E. coli* cells are grown under the conditions described in Example 15 and the inclusion bodies are isolated and purified also as described in Example 15. The pellet containing the inclusion bodies is immediately solubilized in 20 mM HCl pH 2.4 containing 2% glycerol or 2.5 mM mannitol and 1.5 mM lactose by gently stirring for 2 hour at room temperature. After solubilization the inclusion bodies are centrifuged for 20 minutes at 20,000 rpm at 4° C. to remove insoluble material. The supernatant is immediately adjusted to pH 9.5 with NaOH, and is maintained for several hours to overnight at room temperature without disturbing to increase the yield of monomeric protein. Recombinant troponin is then isolated as described in Example 6. Fractions containing troponin are dialyzed against a stabilization buffer containing 30 mM sodium bicarbonate pH 8.0, 10 mM mannitol and 5 mM lactose actose and sodium chloride to raise the osmolality of the preparation to physiological levels. The dialyzed supernatant is filter-sterilized, dispensed in sterile vials and stored at −20° C. The ability of rTN-1 to inhibit bFGF-stimulated capillary EC proliferation is assessed as described in Example 17. The recovered troponin is found to be bioactive and in native state configuration.

EXAMPLE 17
Isolation of Highly Purified Monomeric Troponin I

Recombinant troponin I is expressed in the host cell *E. coli* transfected with plasmid BLS-1 containing the full length of human (Homo sapiens) fast twitch skeletal muscle troponin I. The *E. coli* cells are grown under the conditions described in Example 15 and the inclusion bodies are isolated also as described in Example 15. Troponin is then partially isolated by selective solubilization at acidic pH (4.2–4.8) and by precipitation of contaminant proteins and aggregates by increasing the pH to a less acidic pH (4.2–4.8). The pellet containing the inclusion bodies is solubilized in 20 mM HCl containing 2% glycerol and 1.5 mM lactose by gently stirring for 2 hour at room temperature. After solubilization the inclusion bodies are centrifuged for 20 minutes at 20,000 rpm at 4° C. to remove insoluble material. The supernatant containing monomeric troponin is further purified by selective precipitation of contaminant proteins and aggregates by increasing the pH of the supernatant to pH of about 4.6 with 1 N NaOH accompanied by gently stirring at room temperature. The supernatant is centrifuged for 15 minutes at 20K rpm at 4° C. to remove precipitate. The supernatant containing monomeric troponin is immediately adjusted to pH 9.5 with 1N NaOH. The troponin I, the target peptide, is maintained for several hours to overnight at room temperature without disturbing to increase the yield of monomeric protein. Recombinant troponin is then purified by ion exchange chromatography on Q-SEPHAROSE® (dextran cross-linked agarose), and hydrophobic chromatography on phenyl sepharose followed by a second Q-SEPHAROSE® (dextran cross-linked agarose) column using a sodium chloride gradient. Column effluent fractions containing troponin are dialyzed against a stabilization buffer containing 30 mM sodium bicarbonate pH 8.0, 12 mM mannitol and 6 mM lactose and 0.1 M NaCL to increase the osmolality of the isolated protein to physiological levels. The dialyzed supernatant is filter-sterilized, dispensed in sterile vials and stored at −20° C. The ability of rTN-1 to inhibit bFGF-stimulated capillary EC proliferation is assessed as described in Example 15. The isolated troponin I is found to be bioactive and in native state configuration.

EXAMPLE 18
Removal of Contaminant Proteins by Solubilization of Inclusion Bodies at Elevated pH and Recovery of Monomeric Troponin I Host cells, *E. coli* cells are grown under the conditions described in Example 15 are employed to produce troponin I in inclusion bodies. These are isolated as described in Example 15. Isolation of highly purified monomeric troponin from inclusion bodies is accomplished by solubilizing inclusion bodies in an aqueous solution according to the procedure described in Example 15, followed by lowering the pH of the solution to an acidic pH between about 4.2 to 4.8, in one embodiment to about 4.6–4.7. This drop in pH precipitates contaminant proteins, which are removed by centrifugation. The pH of the solution is then increased to pH 9.5 with 1N NaOH and is maintained for several hours to overnight at room temperature without disturbing to increase the yield of monomeric protein. The supernatant containing troponin I is then transferred into the stabilization buffer according to the procedure described in example 15. The result is bioactive troponin in native state configuration.

EXAMPLE 19

Stabilization of Denatured Troponin I

Recombinant troponin I is expressed in a host cell, *E. coli* harboring plasmid BLS-1 containing the full length of human fast twitch skeletal muscle troponin I. The *E. coli* cells are grown under the conditions described in Example 15 and the inclusion bodies are isolated and purified also as described in Example 15. The final pellet containing the inclusion bodies is immediately solubilized in 20 mM ethanolamine pH 10.3 containing 8 M urea and 0.15 M NaCl for 30 minutes with gently stirring at room temperature. The solubilized protein is then dialyzed to remove urea and salt for 48 hours with a change of buffer after 24 hours at room temperature in 40 mM sodium bicarbonate pH 8.0 containing 20 mM mannitol and 10 mM lactose at a protein concentration between about 2–10 mg/ml. After dialysis the recombinant protein is purified as described in Example 15. Fractions containing highly purified troponin are dialyzed in stabilization buffer containing 30 mM sodium bicarbonate pH 8.0, 12 mM mannitol and 6 mM lactose and 0.1 M NaCl. The dialyzed supernatant is filter-sterilized, dispensed in sterile vials and stored at −20° C. The ability of rTN-1 to inhibit bFGF-stimulated capillary EC proliferation is assessed as described in Example 15.

EXAMPLE 20

Bioassays for Troponin I

The bioactivity and/or therapeutically effective dose of troponin subunits, fragments and analogs produced using methods of the invention can be assayed in vitro or in vitro by various methods.

For example, in assaying for the ability of troponin subunits, fragments, and analogs, to inhibit or interfere with the proliferation of capillary endothelial cells (EC) in vitro, various bioassays known in the art can be used, including but not limited to measuring the incorporation of radioactivity into nucleic acids, calorimetric assays and cell counting.

Inhibition of endothelial cell proliferation may be measured by calorimetric determination of cellular acid phosphatase activity or electronic cell counting. These methods provide a quick and sensitive screen for determining the number of endothelial cells in culture after treatment with the troponin subunit, derivative, or analog of the invention, and an angiogenesis stimulating factor such as aFGF. The calorimetric determination of cellular acid phosphatase activity is described by Connolly et al., *J. Anal. Biochem.* 152:136–140, (1986). According to this method, capillary endothelial cells are treated with angiogenesis stimulating factors, such as aFGF, and a range of potential inhibitor concentrations. These samples are incubated to allow for growth, and then harvested, washed, lysed in a buffer containing a phosphatase substrate, and then incubated a second time. A basic solution is added to stop the reaction and color development is determined with a spectrophotometer at 405 lambda. According to Connolly et al., a linear relationship is obtained between acid phosphatase activity and endothelial cell number up to 10,000 cells/sample. Standard curves for acid phosphatase activity are also generated from known cell numbers in order to confirm that the enzyme levels reflect the actual EC numbers. Percent inhibition is determined by comparing the cell number of samples exposed to stimulus with those exposed to both stimulus and inhibitor.

Troponin bioactivity assessment is disclosed in U.S. Pat. No. 5,837,680, to Moses et al. (1998). Noted is the chick chorioallantoic membrane ("CAM") bioassay. CAM measures the ability of a sample to inhibit the angiogenic process of capillary endothelial cell migration in response to an angiogenic stimulus. In the CAM bioassay, fertilized chick embryos are cultured in Petri dishes. On day 6 of development, a disc of a release polymer, such as methyl cellulose, impregnated with the test sample or an appropriate control substance is placed onto the vascular membrane at its advancing edge. On day 8 of development, the area around the implant is observed and evaluated. Avascular zones surrounding the test implant indicate the presence of an inhibitor of embryonic neovascularization (Moses et al., *Science* 248:1408–1410, 1990; Taylor et al., *Nature* 297:307–312, 1982).

Using the rabbit corneal pocket assay, polymer pellets of ethylene vinyl acetate copolymer ("EVAC") are impregnated with test substance and surgically implanted in a pocket in the rabbit cornea approximately 1 mm from the limbus (Langer et al., *Science* 193:707–72, 1976). To test for an angiogenesis inhibitor, either a piece of carcinoma or some other angiogenic stimulant is implanted distal to the polymer 2 mm from the limbus. In the opposite eye of each rabbit, control polymer pellets that are empty are implanted next to an angiogenic stimulant in the same way. In these control corneas, capillary blood vessels start growing towards the tumor implant in 5–6 days, eventually sweeping over the blank polymer. In test corneas, the directional growth of new capillaries from the limbal blood vessel towards the tumor occurs at a reduced rate and is often inhibited such that an avascular region around the polymer is observed. This assay is quantitated by measurement of the maximum vessel lengths with a stereospecific microscope.

The ability of varying concentrations of troponin subunits, fragments or analogs to interfere with the process of capillary endothelial cell migration in response to an angiogenic stimulus can also be assayed using the modified Boyden chamber technique (see Example 15, and U.S. Pat. No. 5,837,680).

Another assay of troponin subunit, fragment and analog bioactivity, involves the ability of the compounds to inhibit the directed migration of capillary endothelial cells which ultimately result in capillary tube formation. This ability may be assessed for example, using an assay in which capillary endothelial cells plated on collagen gels are challenged with the inhibitor, and determining whether capillary-like tube structures are formed by the cultured endothelial cells.

Mammalian cell expression systems are noted. Reference is made to "Expression of Epstein-Barr virus latent membrane protein 2 in murine fibroblasts by retroviral-mediated gene transfer," Zhu et al., *Zhonghua Shi Yan He Lin Chuang Bing Du Xue Za Zhi* 14(4):342–344 (2000); "Overexpression of bcl-2 inhibits sodium butyrate-induced apoptosis in Chinese hamster ovary cells resulting in enhanced humanized antibody production," Kim et al., *Biotechnol Bioeng*

71(3):184–93 (2000–2001); and "Human and murine immunoglobulin expression vector cassettes," McLean et al. *Mol Immunol*, 37(14):837–45 (2000).

Bacterial expression systems are noted with reference to "Production of active mammalian and viral proteases in bacterial expression systems," Babe et al., *Biotechnol Genet Eng Rev* 17:213–52 (2000).

Known baculovirus and insect cell expression systems include the techniques presented in "Expression of a bioactive bovine interleukin-12 using baculovirus," Takehara et al., *Vet Immunol Immunopathol*, 23;77(1–2):15–25 (2000); "Expression of amiloride-sensitive sodium channel: a strategy for the coexpression of multimeric membrane protein in Sf9 insect cells," Rao et al., *Anal Biochem*, 15;286(2):206–13 (2000); and, "Production monitoring and purification of EBV encoded latent membrane protein 1 expressed and secreted by recombinant baculovirus infected insect cells," Meij et al. *J Virol Methods*, 90(2):193–204 (2000).

Yeast protein expression technology is presented in "Protein expression in yeast; comparison of two expression strategies regarding protein maturation", Schuster et al., *J Biotechnol* 28;84(3):237–48 (2000); and "Non-conventional yeasts as hosts for heterologous protein production," Dominguez et al., *Int Microbiol* 1(2):131–42 (1998).

Fungal expression systems are known in the art. Reference is made to "Cloning and expression of the S-adenosylmethionine decarboxylase gene of Neurospora crassa and processing of its product,." Hoyt et al., *Mol Gen Genet* 263(4):664–73 (2000); "Using DNA-tagged mutagenesis to improve heterologous protein production in *Aspergillus oryzae*," Yaver et al., *Fungal Genet Biol* 2000 Feb; 29(1):28–37; and "Purification, characterization, and heterologous expression in *Fusarium venenatum* of a novel serine carboxypeptidase from *Aspergillus oryzae*," Blinkovsky et al., *Appl Environ Microbiol*, 65(8):3298–303 (1999).

Protein thermostability modification with maintained bioactivity is set forth in "The consensus concept for thermostability engineering of proteins," Lehmann et al. *Biochim Biophys Acta*, 29;1543(2):408–415 (2000).

Particular note is made of labile proteins usefully isolated by the present method. "The acid-labile subunit (ALS) of the 150 kDa IGF-binding protein complex: an important but forgotten component of the circulating IGF system," Boisclair et al, *J Endocrinol*, 170(1):63–70 (2001); "Thermostabilization of a chimeric enzyme by residue substitutions: four amino acid residues in loop regions are responsible for the thermostability of *Thermus thermophilus* isopropylmalate dehydrogenase,"Numata et al., *Biochim Biophys Acta*, 545(1–2):174–83 (2001).

Prion protein expression is addressed in "Nervous and nonnervous cell transduction by recombinant adenoviruses that inducibly express the human prp." Arrabal et al., *Biochem Biophys Res Commun* 285(3):623–32 (2001); and, "Efficient lymphoreticular prion propagation requires prp(c) in stromal and hematopoietic cells, " Kaesser et al. *J Virol*, 75(15):7097–106 (2001). All sources, texts, and publications cited herein are incorporated herein by reference.

Although the foregoing invention has been described in some detail by way of illustration and example for purposes of clarity of understanding, it will be obvious to one skilled in the art that certain changes and modifications may be practiced within the scope of the invention, as limited only by the scope of the appended claims.

What is claimed is:

1. A method for solubilizing and recovering, in bioactive form, a target polypeptide from a host organism in which the target polypeptide is present in insoluble form, which comprises:

disrupting the host cell to produce a lysate;
recovering lysate precipitate containing the target polypeptide; solubilizing the lysate precipitate in a denaturant free, non-buffered solubilization solution producing a solubilization preparation that comprises 1) a concentration of sodium hydroxide between about 8 and about 10 mM and 2) a concentration of polypeptide between about 1 and about 4 mg polypeptide per ml of solubilization solution, wherein the resultant solubilization preparation has a pH of between about 9 and about 11.2.

2. The method of claim 1, wherein the solubilization solution is free of denaturants and detergents.

3. The method of claim 1, further comprising the step of purifying the bioactive target polypeptide.

4. The method of claim 1, where the solubilization preparation has a pH about 10.5 to about 11.2.

5. The method of claim 1, wherein the solubilization preparation comprises sodium hydroxide about 8.0 to about 10 mM.

6. The method of claim 1, wherein the solubilization preparation comprises a concentration of polypeptide about 1.0 to about 4 mg polypeptide per ml of solubilization solution.

7. The method of claim 1, wherein the solubilization solution further comprises a stabilizing compound.

8. The method of claim 7, wherein the stabilizing compound is at concentration between about 1 to about 20 mM.

9. The method of claim 7, wherein the solubilization solution further comprises a second stabilizing compound.

10. The method of claim 7, wherein the stabilizing compound is a stabilizing sugar, stabilizing polyol, stabilizing amino acid or stabilizing polymer.

11. The method of claim 10, wherein the stabilizing polyol is mannitol and the stabilizing sugar is lactose.

12. The method of claim 7, wherein the host organism is bacteria or yeast.

13. The method of claim 1, wherein the host is an *Escherichia coli* cell.

14. The method of claim 13, wherein the host cell is a Yeast cell.

15. The method of claim 1, wherein the target polypeptide is present within the host organism in inclusion bodies.

16. The method of claim 1, wherein the target polypeptide is a protein or a subunit of the protein.

17. The method of claim 1 wherein said target polypeptide is troponin.

18. The method of claim 1 wherein said target polypeptide is troponin 1.

19. A method for solubilizing and recovering, in bioactive and isolated form a target polypeptide from a host organism in which the target polypeptide is present in insoluble form, which comprises:

(a) disrupting the host cell to produce a lysate;
(b) recovering a precipitate containing the target polypeptide from the lysate;
(c) solubilizing the precipitate in a denaturant-free non-buffered solubilization solution to produce a solubilization preparation that comprises
1) hydrogen chloride between 10 and 20 mM; and
2) bioactive target polypeptide between 1 and 4 mg per ml solubilization solution, and
3) pH between 2.0 and 3.0.

20. The method of claim 19, further comprising adjusting the pH of the supernatant to pH 9.5 with NaOH.

21. The method of claim 19, wherein the solubilization solution is free of denaturants and detergents.

22. The method of claim 19, wherein the solubilization preparation has a pH about 2.2 to about 2.8.

23. The method of claim 19, wherein the solubilization preparation comprises a concentration of hydrogen chloride about 10 to about 20 mM.

24. The method of claim 19, wherein the solubilizataon preparation comprises a concentration of polypeptide about 2.5 to about 3 mg polypeptide per ml solubilization solution.

25. The method of claim 19, wherein the solubilization preparation comprises a concentration of polypeptide about 1.8 to about 2 mg polypeptide per ml solubilization solution.

26. The method of claim 19, wherein the solubiization solution further comprises a stabilizing compound.

27. The method of claim 26, wherein the stabilizing compound is at concentration about 1 to about 20 mM.

28. The method of claim 26, wherein the solubilization solution further comprises a second stabilizing compound.

29. The method of claim 26, wherein the stabilizing compound is a sugar, polyol, amino acid or polymer.

30. The method of claim 26, wherein the stabilizing compound is mannitol and lactose.

31. The method of claim 19, wherein the host cell is bacteria or yeast.

32. The method of claim 31, wherein the host cell is an *Escherichia coli* cell.

33. The method of claim 31, wherein the host cell is a *Saccharomyces* cell.

34. The method of claim 31, wherein the heterologous polypeptide is present within inclusion bodies within the host cell.

35. A method for isolating recombinant polypeptides comprising:

providing a non-buffered solution containing a stabilizing compound and hydrogen chloride between 10 and 20 mM;

producing a polypeptide solution about 1 to about 4 mg polypeptide per ml by adding to the non-buffered denaturant free solution an insoluble recombinant polypeptide, wherein the polypeptide solution has a pH about 2.0 to about 3.0;

increasing the pH of the polypeptide solution to between about 4 and 5 using 1N NaOH;

centrifuging the polypeptide solution and recovering precipitate-free supernatant;

adjusting the pH of the supernatant to about pH 9 to about 10.5 with 1N NaOH; and retaining the supernatant comprising isolated target polypeptide.

36. A method for isolating recombinant polypeptides comprising:

providing a non-buffered solution containing a stabilizing compound and sodium hydroxide about 8 to about 10 mM;

producing a polypeptide solution about 1 to about 4 mg polypeptide per ml by adding to the non-buffered denaturant free solution an insoluble recombinant polypeptide, wherein the polypeptide solution has a pH about 9 to about 11.2;

lowering the pH of the polypeptide solution to about 4 to 5 using 1N NaOH;

centrifuging the polypeptide solution and recovering precipitate-free supernatant;

adjusting the pH of the supernatant to pH of about 9 to about 10.5 with 1N NaOH; and retaining the supernatant comprising isolated target polypeptide at least about 10% more pure than the isolated target polypeptide in insoluble form.

37. A method for preparing bioactive recombinant polypeptide that has been denatured in a chaotrope-containing solution, comprising:

decreasing the concentration of the chaotropic agent in the chaotrope-containing solution by dialyzing the chaotrope-containing solution against a renaturing buffer of pH of about 9 to about 10.5 and buffer concentration of about 10 to about 50 mM, wherein the renaturing buffer further contains a stabilizing compound.

38. The method of claim 37, wherein the stabilizing compound is a sugar or polyol.

39. The method of claim 37, wherein the stabilizing compound is a sugar about 2 to about 12 mM.

40. The method of claim 37, wherein the stabilizing compound is a polyol about 5 to about 100 mM.

\* \* \* \* \*